United States Patent
Tajima et al.

(10) Patent No.: US 9,629,601 B2
(45) Date of Patent: Apr. 25, 2017

(54) RADIATION IMAGE DETECTING DEVICE AND RADIATION IMAGING SYSTEM

(71) Applicant: FUJIFILM CORPORATION, Tokyo (JP)

(72) Inventors: Takashi Tajima, Ashigarakami-gun (JP); Takeshi Kuwabara, Ashigarakami-gun (JP); Yusuke Kitagawa, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 270 days.

(21) Appl. No.: 14/516,625

(22) Filed: Oct. 17, 2014

(65) Prior Publication Data
US 2015/0036802 A1    Feb. 5, 2015

Related U.S. Application Data

(63) Continuation of application No. PCT/JP2013/060920, filed on Apr. 11, 2013.

(30) Foreign Application Priority Data

Apr. 20, 2012  (JP) ................................. 2012-096276

(51) Int. Cl.
G01N 23/04      (2006.01)
A61B 6/00       (2006.01)
G01T 1/08       (2006.01)

(52) U.S. Cl.
CPC ............ *A61B 6/542* (2013.01); *A61B 6/4208* (2013.01); *A61B 6/4291* (2013.01); *G01T 1/08* (2013.01); *A61B 6/4233* (2013.01); *A61B 6/4283* (2013.01)

(58) Field of Classification Search
CPC ..... A61B 6/542; A61B 6/4291; A61B 6/4233; A61B 6/4208; G01T 1/08
(Continued)

(56) References Cited

U.S. PATENT DOCUMENTS

| 6,944,266 B2 | 9/2005 | Yamazaki et al. |
| 6,952,465 B2 | 10/2005 | Hirai et al. |
| 2004/0096035 A1* | 5/2004 | Yamazaki .............. A61B 6/107 378/97 |

OTHER PUBLICATIONS

International Preliminary Report on Patentability and English translation of the Written Opinion of the International Searching Authority (Forms PCT/IB/338, PCT/IB/373 and PCT/ISA/237), dated Oct. 30, 2014, for International Application No. PCT/JP2013/060920.
(Continued)

*Primary Examiner* — Courtney Thomas
(74) *Attorney, Agent, or Firm* — Birch, Stewart, Kolasch & Birch, LLP

(57) ABSTRACT

In a detection panel, plural pixels which receive X-ray and accumulate electric charge and plural measuring pixels which detect X-ray dose are provided on an imaging surface. The plural measuring pixels are arranged periodically with an interval. In a position facing to the imaging surface, there is a grid where X-ray absorbing sections and X-ray transmitting sections are arranged in a periodic alternating manner in a first direction. Since the arrangement period of the measuring pixels in the first direction is different from a fluctuation period of grid detection signals obtained when the grid is photographed by the detection panel, output values of the plurality of measuring pixels disperse and a fluctuation range of average values is suppressed.

15 Claims, 24 Drawing Sheets

(58) Field of Classification Search
USPC .............................. 378/62, 95–98, 145–155
See application file for complete search history.

(56) References Cited

OTHER PUBLICATIONS

International Search Report issued in PCT/JP2013/060920, mailed on May 14, 2013.
Written Opinion issued in PCT/JP2013/060920, mailed on May 14, 2013.

* cited by examiner

FIG. 16
| BODY PART TO BE IMAGED | TUBE VOLTAGE (kV) | TUBE CURRENT (mA) | MEASUREMENT AREA | EMISSION STOP THRESHOLD VALUE |
|---|---|---|---|---|
| ... | ... | ... | ... | ... |
| CHEST | V1 | I1 |  | th1 |
| ABDOMEN | V2 | I2 |  | th2 |
| ... | ... | ... | ... | ... |

RADIATION IMAGE DETECTING DEVICE AND RADIATION IMAGING SYSTEM

CROSS-REFERENCE TO RELATED APPLICATIONS

This application is a Continuation of PCT International Application No. PCT/JP2013/060920 filed on Apr. 11, 2013, which claims priority under 35 U.S.C. §119 to Japanese Patent Application No. 2012-096276, filed Apr. 20, 2012. Each of the above application(s) is hereby expressly incorporated by reference, in its entirety, into the present application.

BACKGROUND OF THE INVENTION

1. Field of the Invention

The present invention relates to a radiation image detecting device comprising a dose measuring sensor for an exposure control of a radiation image, and a radiation imaging system using this device.

2. Description Related to the Prior Art

In a medical field, an X-ray imaging system using radiation, e.g., X-ray is known. The X-ray imaging system comprises an X-ray generating device for generating X-ray and an X-ray imaging device for producing an X-ray image of an object (patient) with X-ray which penetrated the object. The X-ray generating device includes an X-ray source for irradiating X-ray toward the object, a source controller for controlling the X-ray source, and an emission switch for inputting a command to the source controller so as to activate the X-ray source. The X-ray imaging device includes an X-ray image detecting device for detecting the X-ray image based on X-ray which penetrated the object, and a console for controlling the X-ray image detecting device and for saving and displaying the X-ray image.

As the X-ray image detecting device, one with an image detection section (which is called a flat panel detector (FPD)) is in widespread use. The image detection section has a detection panel having imaging surface where pixels which accumulate electric charge according to an incident quantity of X-ray was arranged into a matrix, and a circuitry part for driving the detection panel. The image detection section detects an X-ray image as electric signals. The detection panel detects an X-ray image of an object by accumulating electric charge of each pixel and converting the accumulated electric charge into a voltage signal in a signal processing circuit. The detected X-ray image is output as digital image data. There also exists a portable type of X-ray image detecting device, which is called an electronic cassette.

In X-ray photography, to reduce an influence of scattered radiation which occurs when X-ray penetrates an object, an anti-scatter member called a grid may be located between the object and the X-ray image detecting device for the photography. The grid is formed of alternate arrangement of X-ray absorbing sections and X-ray transmitting sections each of which is formed into a slim strip shape. The X-ray absorbing section is made of a material such as lead, which absorbs and hardly transmits X-ray. The X-ray transmitting section is made of a material such as aluminum, which is capable of transmitting X-ray. Since the X-ray absorbing sections and the X-ray transmitting sections are arranged alternately in a single direction, a striped pattern is formed by these sections. By placing the grid between the imaging surface of the detection panel and an object, most of the scattered radiation is absorbed in the X-ray absorbing section in the grid before arriving at the imaging surface. Accordingly, an image having high contrast with a little influence of scattered radiation can be obtained. The grid is attached to an imaging stand, a housing of the X-ray image detecting device, or the like.

In addition, as one of items to classify a type of grid, there is a grid density representing the number of X-ray absorbing sections per unit width. For example, there are various types of grids having a grid density in a range of 26 lines/cm-100 lines/cm. In case that the grid density is 40 lines/cm (4 lines/mm), the grid pitch becomes 250 μm. The grid pitch is the width of one set of the X-ray absorbing section and the X-ray transmitting section.

Some of the X-ray image detecting device has an automatic exposure control (AEC) function. In the AEC, irradiation of X-ray from the X-ray source is stopped and exposure of an X-ray image is controlled when a dose of irradiated X-ray from the X-ray source reached the predetermined emission stop threshold value (e.g., U.S. Pat. Nos. 6,952,465 and 6,944,266). Such the X-ray image detecting device is provided with dose measuring sensors for detecting a dose of X-ray penetrated through an object and outputting a signal depending on the dose.

The U.S. Pat. No. 6,952,465 describes an X-ray image detecting device which provides dose measuring sensors of a stripe shape with the length for 500 pixels separately from pixels in an imaging surface of a detection panel. In the U.S. Pat. No. 6,952,465, the dose measuring sensors are arranged so that a longitudinal direction (direction of the stripe) of the dose measuring sensors of the stripe shape and a course of a stripe of a grid become non-parallel (for example, at right angles). Accordingly, even in case that a gap occurs in the geometric layout of the grid and the dose measuring sensors (relative positional relations of the grid and the dose measuring sensors), fluctuation of output value of the signal which the dose measuring sensor outputs can be suppressed to perform stable AEC.

The dose measuring sensors are provided in the imaging surface. Accordingly, production errors and installation backlash of the grid cause position gaps in the geometric layout with the grid and the dose measuring sensors. Each of the X-ray absorbing section and the X-ray transmitting section of the grid has a width of μm order. Accordingly, production errors and installation backlash of the grid easily make position gaps between the grid and the dose measuring sensors, in the degree of about the width of one of the X-ray absorbing sections and the X-ray transmitting sections. When position gaps in the geometric layout with the grid occur, an incident quantity of X-ray to the dose measuring sensors fluctuates even if an exposure dose of X-ray is the same. Accordingly, the output value of the dose measuring sensors fluctuates. A fluctuation range of the output value of the dose measuring sensors becomes greatest when the direction of the stripe of the grid is parallel to the direction of the stripe of the dose measuring sensors.

In case that the direction of the stripe of the grid is parallel to the direction of the stripe of the dose measuring sensors, the dose measuring sensor of the stripe shape may be covered by the X-ray absorbing section across the whole of the longitudinal direction, or may be covered by the X-ray transmitting section in the same way. When the whole area of the dose measuring sensor hides behind the X-ray absorbing section, an incident quantity of X-ray decreases in the whole area of the dose measuring sensor. Accordingly, output value of the dose measuring sensor is minimized. Conversely, even if an exposure dose of X-ray is the same, when the whole area of the dose measuring sensor hides behind the X-ray transmitting section, an incident quantity of X-ray increases in the whole area of the dose measuring sensor. Accordingly, output value of the dose measuring sensor is maximized. In this way, when the direction of the stripe of the dose measuring sensors and the direction of the stripe of the grid are collimated, a fluctuation range of the output value of the dose measuring sensors caused by the position gap of the geometric layout of the grid and the dose measuring sensors increases.

In consideration of this problem, in the U.S. Pat. No. 6,952,465, dose measuring sensors in a stripe shape are arranged in non-parallel with a direction of a stripe of a grid. Even when position gaps occur in the geometric layout of the grid and the dose measuring sensors, a part of the dose measuring sensor is always located behind the X-ray absorbing section, and the other part is located behind the X-ray transmitting section. In this configuration, an incident quantity of X-ray relatively lowers in apart of the dose measuring sensor. However, since an incident quantity of X-ray relatively increases in the other part of the dose measuring sensor, the output value of the dose measuring sensor is equalized. Therefore, in comparison with the case that the stripe direction of the dose measuring sensors are parallel to the stripe direction of the grid, a fluctuation range of the output value of the dose measuring sensors caused by the position gap of the geometric layout of the grid and the dose measuring sensors can be reduced. Accordingly, stable AEC can be realized.

In an embodiment of the U.S. Pat. No. 6,952,465, a size of pixels is 105 μm×105 μm, and dose measuring sensors have a length for 500 pixels. Accordingly, the length of the dose measuring sensors is about 105 μm×500=52,500 μm (approximately 50 mm). The dose measuring sensors replace some pixels or are placed between adjacent pixels. In case that the dose measuring sensors are placed between pixels, a size of pixels adjacent to the dose measuring sensors is reduced to make places for the dose measuring sensors. In this way, the plural dose measuring sensors are placed in predetermined areas.

In addition, in an X-ray image detecting device described in the U.S. Pat. No. 6,944,266, as a substitute for dose measuring sensors of a stripe shape, a part of pixels in an imaging surface is assigned as measuring pixels functioning as dose measuring sensors (referred to as AEC pixels in U.S. Pat. No. 6,944,266). The pixels of U.S. Pat. No. 6,944,266 can perform so-called non destructive read-out, in which output value is retrieved with holding the accumulated electric charge. The measuring pixels also can perform non destructive read-out.

In the X-ray image detecting device of the U.S. Pat. No. 6,944,266, the measuring pixels are placed in an imaging surface. Accordingly, like the U.S. Pat. No. 6,952,465, output values of the measuring pixels fluctuate by the position gap of the geometric layout of a grid and the measuring pixels. To deal with the problem that output value of the each measuring pixel fluctuates in the U.S. Pat. No. 6,944,266, a calibration of the output value of the each measuring pixel is carried out.

Specifically, in the U.S. Pat. No. 6,944,266, before object photography, X-ray is uniformly irradiated to the imaging surface to which the grid was attached, so as to obtain a gain image representing output value of the each measuring pixel in the imaging surface. The gain image reflects a fluctuation of the output value of the each measuring pixel to which the grid was attached. And in AEC for object photography, an output value of the each measuring pixel is corrected by applying calibration based on the gain image to the output value output from the each measuring pixel. The output value of each measuring pixel fluctuates by not only the type of the grid such as the grid density but also imaging conditions including a dose of X-ray, radiation quality depending on tube voltage, and so on. In addition, even in case that the type of the grid and imaging conditions are the same, since production errors and installation backlash of the grid cause position gaps in the geometric layout with the grid and the measuring pixels, the acquisition of gain image is carried out for every photography.

In the U.S. Pat. No. 6,952,465, spaces for the dose measuring sensors of stripe shape are secured by substitution of pixels and reduction of the pixel size. Accordingly, in photographed X-ray image, the density of area where dose measuring sensors are located decreases. Since density difference between the area where the dose measuring sensors are located and the adjacent area, a line-formed density step appears. Since the length of the dose measuring sensor of stripe shape is approximately 50 mm which is visible by human eye, the density step of the X-ray image becomes a degree highly visible by human eye. The U.S. Pat. No. 6,952,465 discloses that dose measuring sensors are considered to be defect pixels and a defect correction is carried out to cancel such a density step. However, to carry out the defect correction, an additional process to prepare correction data is required. Furthermore, it is difficult to cancel the defect to the degree that the defect is not visible even if the defect correction is carried out, because the dose measuring sensor has the large size of approximately 50 mm. Accordingly, there is a concern that the quality of the X-ray image will decrease.

The U.S. Pat. No. 6,944,266 uses a part of the pixels as the measuring pixels, and output value of the measuring pixel is obtained through non destructive read-out. Accordingly, the density step such as in the U.S. Pat. No. 6,952,465 does not occur in the X-ray image. Therefore there are not the problem that an additional process is required for the defect correction and the problem of quality deterioration of the X-ray image. However, the X-ray image detecting device of the U.S. Pat. No. 6,944,266 must acquire a gain image for each photography. This brings another problem that it should take time and require additional process for obtaining the gain image. Furthermore, appropriate correction is not possible even if the acquired gain image is used, in case that position gaps in the geometric layout with the grid and the measuring pixels are occurred by a shock or other causes before performing the object photography after acquiring the gain image.

SUMMARY OF THE INVENTION

An object of the present invention is to provide a radiation image detecting device and a radiation imaging system in which stable AEC can be performed without influence of position gaps in the geometric layout of a grid and dose measuring sensors, with little concern of image quality deterioration and no addition of complex processes.

To achieve the above and other objects, a radiation image detecting device of the present invention comprises a detection panel and a plurality of dose measuring sensors. For photography, an anti-scatter grid where radiation absorbing sections and radiation transmitting sections are arranged in a periodic alternating manner in a first direction is used. The radiation absorbing section absorbs radiation, and the radiation transmitting section penetrates radiation. The detection panel has an imaging surface where plural pixels for receiving radiation from a radiation source are provided, and a radiation image of an object is detected by the pixels receiving radiation which penetrated the object. The plural dose measuring sensors are provided to perform exposure control of the radiation image. The dose measuring sensors are arranged in the imaging surface in the first direction periodically with keeping a space, and detect radiation dose which penetrated the object to output a signal depending on the dose. A fluctuation period of a grid detection signal is different from an arrangement period of the plural dose measuring sensors in the first direction in the imaging surface. The grid detection signal represents an image of the anti-scatter grid which is obtained when radiation is irradiated equally to the imaging surface and the anti-scatter grid is photographed by the detection panel. The output value of the grid detection signal fluctuates periodically by reflecting an arrangement state in the first direction of the radiation absorbing section and the radiation transmitting section.

It is preferable that the arrangement period of the dose measuring sensors is not an integral multiple of the fluctuation period of the grid detection signal.

It is preferable that the arrangement period of the dose measuring sensors and the fluctuation period of the grid detection signal are relatively prime.

It is preferable that the arrangement period of the dose measuring sensors is different from the fluctuation period of the grid detection signal also in a second direction which is perpendicular to the first direction. Regarding the dose measuring sensors, it is preferable that the arrangement period in the first direction and the arrangement period in the second direction are the same.

The minimum size of the single dose measuring sensor is the same as for example a size of the pixel in the imaging surface. In addition, a pixel pitch of the pixels is larger than half of a grid pitch which is the width of one set of the radiation absorbing section and the radiation transmitting section in the anti-scatter grid.

For example, the dose measuring sensors are measuring pixels using a part of the pixels. In case that the plural measuring pixels are arranged in a line direction corresponding to the first direction and a column direction corresponding to the second direction with an interval corresponding to at least one line or one column in the each direction, the arrangement period in the first direction is an interval length in the line direction, and the arrangement period in the second direction is an interval length in the column direction. The single dose measuring sensor may be a measuring pixel group consisting of a plurality of the adjacent measuring pixels. In this case, the arrangement period is an arrangement period of the plural measuring pixel groups which are arranged periodically with an interval.

The dose measuring sensor outputs a signal corresponding to a dose per unit time. And it is preferable that the radiation image detecting device comprises an automatic exposure controller. The automatic exposure controller multiplies output value from the dose measuring sensors, compares the multiplied integrated value with a predetermined emission stop threshold value, and stops irradiation of radiation from the radiation source when the integrated value reaches the emission stop threshold value. Automatic exposure controller calculates the average value of output value from the plural dose measuring sensors, and multiplies the calculated average value to obtain the integrated value.

It is preferable that the anti-scatter grid is detachably attached to the radiation image detecting device.

A radiation imaging system of the present invention comprises a radiation generator including a radiation source for irradiating radiation and a radiation image detecting device for detecting a radiation image. For photography, an anti-scatter grid where radiation absorbing sections and radiation transmitting sections are arranged in a periodic alternating manner in a first direction is used. The radiation image detecting device includes a detection panel and plural dose measuring sensors. The detection panel has an imaging surface where plural pixels for receiving radiation from a radiation source are provided, and a radiation image of an object is detected by the pixels receiving radiation which penetrated the object. The plural dose measuring sensors are provided to perform exposure control of the radiation image. The dose measuring sensors are arranged in the imaging surface in the first direction periodically with keeping a space, and detect radiation dose which penetrated the object to output a signal depending on the dose. A fluctuation period of a grid detection signal is different from an arrangement period of the plural dose measuring sensors in the first direction in the imaging surface. The grid detection signal expresses an image of the anti-scatter grid which is obtained when radiation is irradiated equally to the imaging surface and the anti-scatter grid is photographed by the detection panel. The output value of the grid detection signal fluctuates periodically by reflecting an arrangement state in the first direction of the radiation absorbing section and the radiation transmitting section.

According to the present invention, the arrangement period of the plural dose measuring sensors arranged in the imaging surface with the interval is different from the fluctuation period of the output value of the grid detection signal representing the image of anti-scatter grid which is obtained when radiation is irradiated equally to the imaging surface and the anti-scatter grid is photographed by the detection panel. Accordingly, it never occurs that all of the plural dose measuring sensors are located at the position corresponding to the maximum output value or the minimum output value of the grid detection signal. Therefore, there is little concern for deterioration of image quality. In addition, stable AEC can be performed without influence of position gaps in the geometric layout of the grid and the dose measuring sensors, with no addition of complex processes.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 16 is a table of imaging conditions set in the console;

DESCRIPTION OF THE PREFERRED EMBODIMENTS

[First Embodiment]

Figure 1:
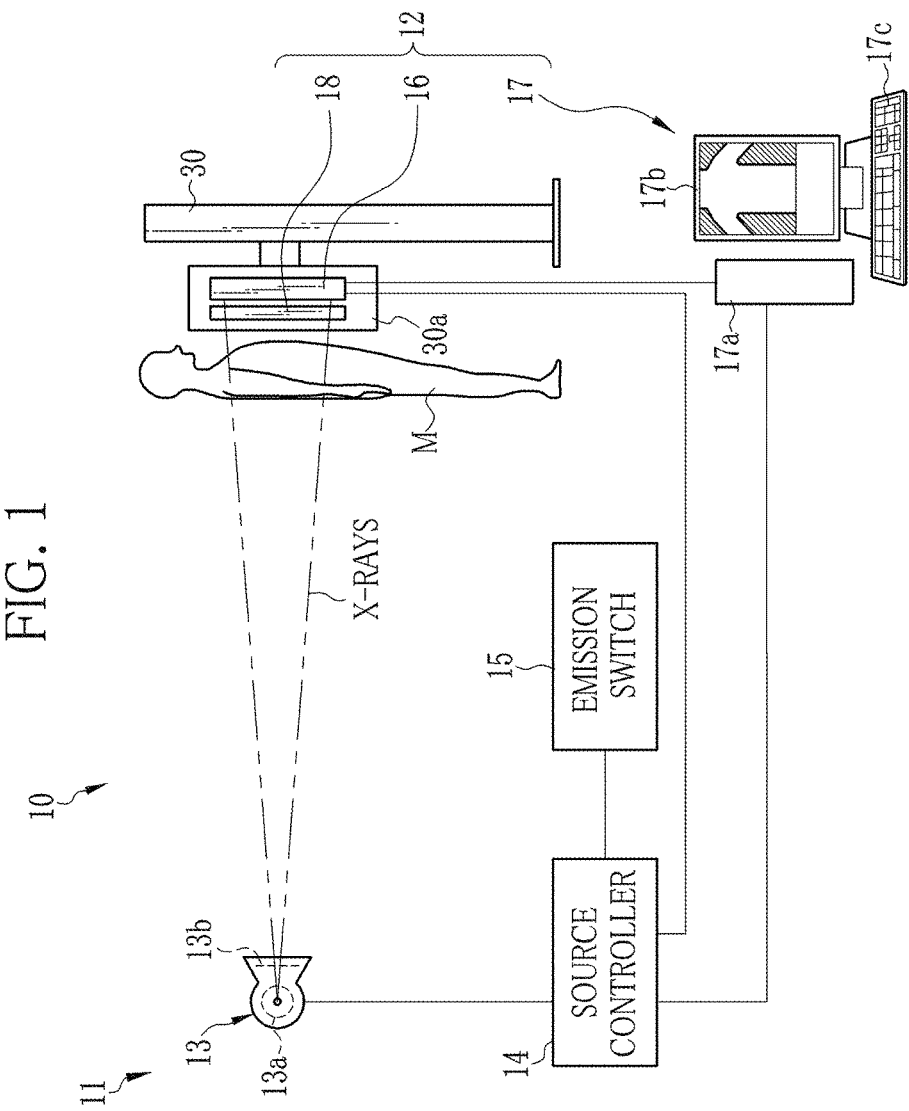
FIG. 1 is a schematic view of an X-ray imaging system.

As shown in FIG. 1, an X-ray imaging system 10 is constituted of an X-ray generating device 11 for generating X-rays and an X-ray imaging device 12 for producing an X-ray image from the X-rays passed through a patient M (an object). The X-ray generating device 11 includes an X-ray source 13 for emitting X-rays, a source controller 14 for controlling the X-ray source 13, and an emission switch 15 for commanding the start of X-ray emission. The X-ray imaging device 12 includes an electronic cassette 16 which is a portable type X-ray image detecting device, a console 17 for controlling the electronic cassette 16, and an imaging stand 30. The source controller 14, the electronic cassette 16, and the console 17 are communicably connected to each other through a wired or wireless communication unit.

The electronic cassette 16 can be detachably attached to the imaging stand 30 which is in a standing position. The electronic cassette 16 includes an image detection section 35 (see FIG. 4) having a detection panel 35a where an imaging surface 36 was formed and a rectangular flat box (not illustrated) of a portable type accommodating the image detection section 35. The plane geometry of the electronic cassette 16 of this embodiment is, for example, four-square, in which the size of length and breadth is the same.

The electronic cassette 16 is detachably set on a holder 30a of an imaging stand 30 in such a position that the imaging surface 36 of the detection panel 35a is opposed to the X-ray source 13. In addition, the electronic cassette 16 is usable by itself in a state of being put on a bed under the patient M lying, or being held by the patient M himself/herself.

In addition, the X-ray imaging device 12 can perform photographing with use of an anti-scatter grid (hereinafter referred as the grid) 18 removing scattered radiation which occurs when X-ray penetrates the patient M. The grid 18 is a thin plate having almost the same size of the electronic cassette 16, and can be detachably attached to the holder 30a of the imaging stand 30, with the electronic cassette 16. The grid 18 is placed in the holder 30a with facing the imaging surface 36 of the electronic cassette 16. Accordingly, at the time of the photography, the grid 18 is located between the patient M and the electronic cassette 16.

Since the grid 18 is detachably attached to the holder 30a, the grid 18 can be changed depending on a purpose of photography or removed from the holder 30a for the X-ray photography. The holder 30a does not have a device for swinging the grid 18. Accordingly, the grid 18 is a so-called standstill grid which is fixed in a setting position for being used. Note that the grid 18 may be detachably attached to the electronic cassette 16. Also in this case, the grid 18 can be changed depending on a purpose of photography or removed from the holder 30a for photography.

The X-ray source 13 has an X-ray tube 13a for emitting X-rays and a collimator 13b for limiting an irradiation field of X-rays. The X-ray tube 13a has a cathode being a filament for emitting thermoelectrons and an anode (target) that radiates X-rays by collision of the thermoelectrons emitted from the cathode. The collimator 13b is composed of, for example, four X-ray shielding lead plates disposed on each side of a rectangle so as to form an irradiation opening in its middle through which the X-rays propagate. A shift of the lead plates varies the size of the irradiation opening to limit the irradiation field.

Figure 2:
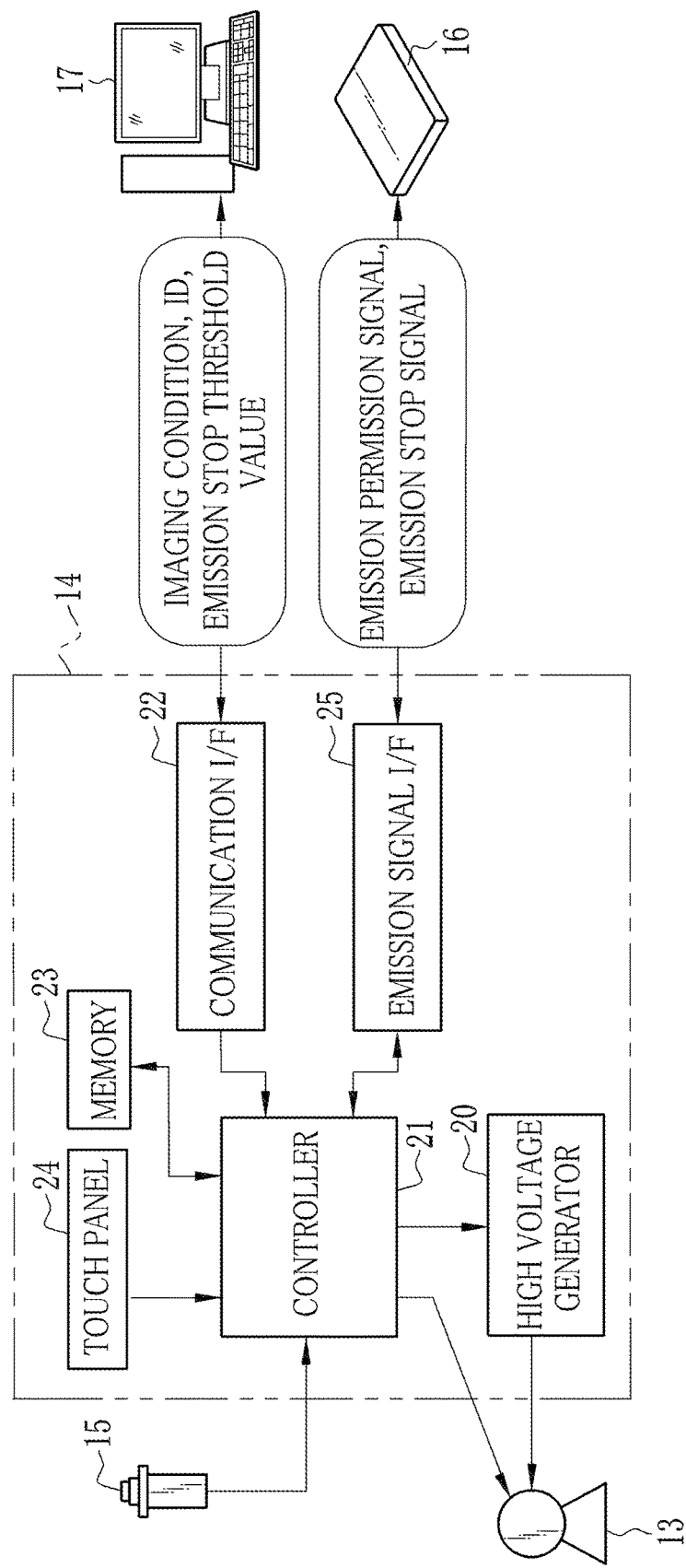
FIG. 2 is a block diagram of a source controller.

As shown in FIG. 2, the source controller 14 includes a high voltage generator 20, a controller 21, and a communication I/F 22. The high voltage generator 20 generates high tube voltage by multiplying input voltage by a transformer, and supplies the tube voltage to the X-ray source 13 through a high voltage cable. The controller 21 controls tube voltage for determining an energy spectrum of X-rays emitted from the X-ray source 13, tube current for determining an emission amount per unit of time, and X-ray emission time. The communication I/F 22 mediates transmission of information and signals from and to the console 17.

The emission switch 15, a memory 23, and a touch panel 24 are connected to the controller 21. The emission switch 15 is a switch operated by an operator such as a radiological technician at the start of imaging, and is a two-step push button switch, for example. Upon a half-press of the emission switch 15, a warm-up start signal is issued to start warming up the X-ray source 13. Upon a full-press, an emission start signal is issued to start X-ray emission from the X-ray source 13. These signals are inputted to the source controller 14 through a signal cable. Upon receiving the emission start signal from the emission switch 15, the controller 21 starts electric power supply from the high voltage generator 20 to the X-ray source 13.

Several types of imaging conditions each including a tube voltage, a tube current, an emission time and/or a tube current-time product (mAs) are stored in advance in the memory 23. The operator manually sets an appropriate imaging condition from the several types of imaging conditions through the touch panel 24. The source controller 14 starts emission control of X-rays based on the tube voltage, the tube current, the emission time and/or the tube current-time product of the set imaging condition. The electronic cassette 16 is provided with an AEC function, which detects a dose per unit time of irradiated X-ray from the X-ray source 13. When it is detected that the applied X-ray dose has reached a required value, the AEC function stops the X-ray emission even if the emission time or the tube current-time product has not yet reached the set value.

To prevent the dose shortage by X-ray emission being finished before reached the required value and the AEC function judging to stop the emission, value of the emission time or the tube current-time product set in the source controller 14 has a margin. The maximal value of emission time set according to the safety regulations depending on a photography site may be set in the source controller 14. The imaging condition may be transmitted from the console 17 through the communication I/F 22.

An emission signal I/F 25 is connected to the electronic cassette 16 to use the AEC function. In this case, upon receiving the warm-up start signal from the emission switch 15, the controller 21 transmits an emission start request signal to the electronic cassette 16 through the emission signal I/F 25. In response to the emission start request signal, the electronic cassette 16 performs a preparation process. The electronic cassette 16 transmits the emission permission signal to the source controller 14 when the preparation process is completed and the photography became available. Upon receiving the emission permission signal from the electronic cassette 16 at the emission signal I/F 25 and further receiving the emission start signal from the emission switch 15, the controller 21 starts electric power supply from the high voltage generator 20 to the X-ray source 13 to start X-ray emission. Upon receiving the emission stop signal by the emission signal I/F 25, the controller 21 stops the electric power supply from the high voltage generator 20 to the X-ray source 13 to stop the X-ray emission. The controller 21 has a timer used for stopping the X-ray emission when the set emission time has elapsed, in addition to the function of stopping the X-ray emission in response to the emission stop signal.

Figure 3:
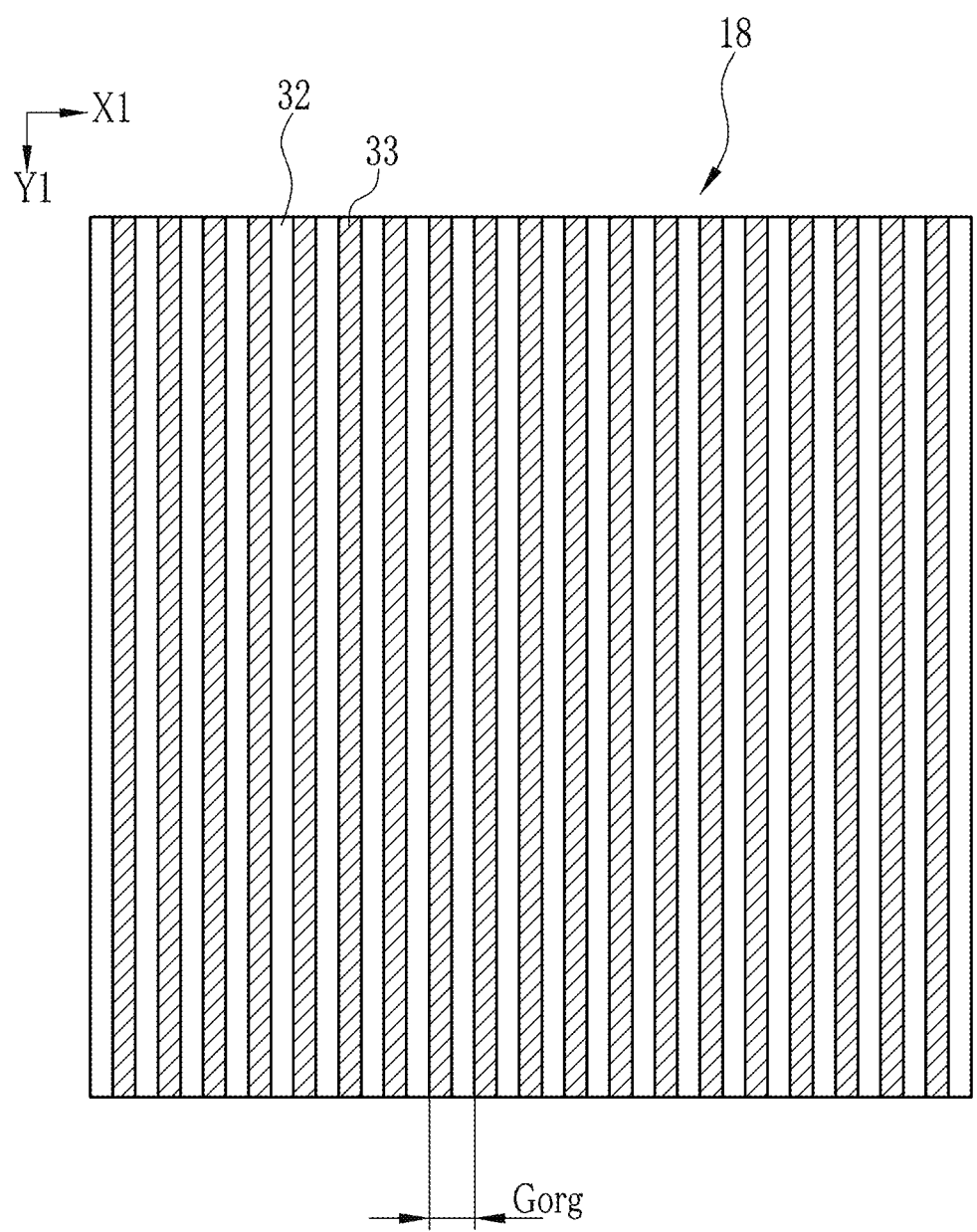
FIG. 3 is an explanatory view of a configuration of a grid.

As illustrated in FIG. 3, the grid 18 has approximately the same size and shape with the electronic cassette 16. The grid 18 has strip-shaped X-ray transmitting sections 32 extending in Y1 direction equivalent to the second direction of the present invention and X-ray absorbing sections 33 illustrated by hatching. These sections 32 and 33 are in alternative arrangement along X1 direction which is at right angles to Y1 direction and is equivalent to the first direction of the present invention. The X-ray transmitting section 32 is formed of a material which is easy to penetrate X-ray, for example aluminum. The X-ray absorbing section 33 is formed of a material which has high shielding characteristics of X-ray and is easy to absorb X-ray, for example lead, molybdenum alloying, tantalum alloying and so on. The grid 18 prevents decreasing of a contrast of an X-ray image caused by scattered radiation which occurs when X-ray penetrates the patient M, by the X-ray absorbing section 33 absorbing the scattered radiation.

Figure 4:
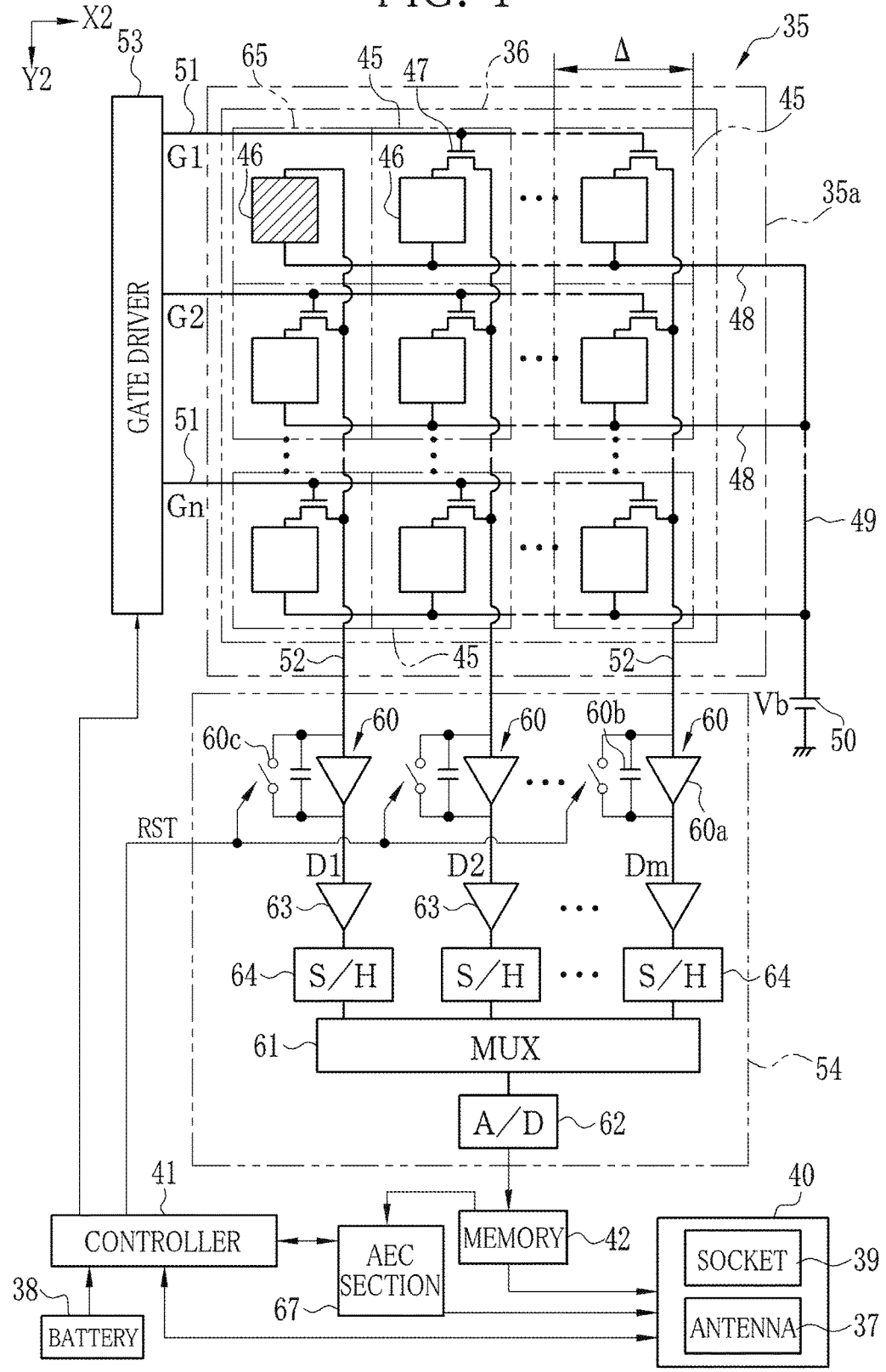
FIG. 4 is a block diagram of an electronic cassette.

The grid 18 is attached to the holder 30a such that the X1 direction which is the arrangement direction of the X-ray transmitting sections 32 and the X-ray absorbing sections 33 accords with the line direction X2 of pixels 45 (see FIG. 4).

Regarding the grid 18, there are various kinds of the grid for example in the range of 26 lines/cm to 100 lines/cm of grid density, which expresses the number of the X-ray absorbing sections 33 per unit width in the arrangement direction of the X-ray transmitting sections 32 and the X-ray absorbing section 33 (X1 direction). In this embodiment, the grid having a grid density of 40 lines/cm (4 lines/mm), which is general in X-ray photography, is used. Total width of the X-ray transmitting section 32 and the X-ray absorbing section 33 in the X1 direction is the grid pitch Gorg. In case the grid density is 4 lines/mm, the grid pitch Gorg is 250 µm.

As illustrated in FIG. 4, the electronic cassette 16 contains in the above-described housing the image detection section 35 having the detection panel 35a, an antenna 37 and a battery 38. The electronic cassette 16 enables wireless communication with the console 17 through use of the antenna 37 and the battery 38. The antenna 37 transmits and receives a radio wave for the wireless communication to and from the console 17. The battery 38 supplies electric power to each component of the electronic cassette 16. The battery 38 is small enough to be contained in the slim electronic cassette 16. The battery 38 can be taken out of the electronic cassette 16 and mounted on a dedicated cradle for recharging. Alternatively, the battery 38 may be configured to be recharged by a wireless power feeder.

In addition to the antenna 37, the electronic cassette 16 is provided with a socket 39. The socket 39 is used for establishing wired communication with the console 17, in such a case where the wireless communication between the electronic cassette 16 and the console 17 is disabled due to a shortage of the battery 38 or the like. Connecting a cable of the console 17 to the socket 39 enables the wired communication with the console 17. At this time, the console 17 may feed the electric power to the electronic cassette 16 through the power circuit 68.

The antenna 37 and the socket 39 are provided in a communication unit 40. The communication unit 40 mediates transmission and reception of various types of information and signals including image data among the antenna 37 or the socket 39, a controller 41, and a memory 42.

The image detection section 35 includes the detection panel 35a and a circuitry part for controlling drive of the detection panel 35a. The detection panel 35a has the imaging surface 36 that has a TFT (Thin Film Transistor) active matrix substrate and a plurality of pixels 45 which are arranged on the TFT active matrix substrate in two dimensions. Each of the pixels 45 produces electric charge in accordance with the amount of X-rays incident thereon. The plurality of pixels 45 are arranged in a matrix of n rows (X2 direction) and m columns (Y2 direction) at a predetermined pitch. The detection panel 35a has a plane geometry of square shape, the size of the imaging surface 36 is for example 430 mm×430 mm, and the number of the pixels is 2,880×2,880. The pixels 45 are square pixels in which the size of length and width is the same, and the size of the pixels 45 is 150 µm×150 µm. The size of length and width of the pixels 45 is equivalent to the pixels pitch Δ in each of the X2 direction and the Y2 direction.

The detection panel 35a is of an indirect conversion type, having a scintillator (phosphor, not illustrated) for converting the X-rays into visible light. The pixels 45 perform photoelectric conversion of the visible light produced by the scintillator. The scintillator is made of CsI:Tl (thallium-activated cesium iodide), GOS ($Gd_2O_2S$:Tb, terbium-activated gadolinium oxysulfide), or the like, and is opposed to the entire imaging surface 36 on which the pixels 45 are arranged. The scintillator and the TFT active matrix substrate may adopt either a PSS (penetration side sampling) method or an ISS (irradiation side sampling) method. In the PSS method, the scintillator and the substrate are disposed in this order from an X-ray incident side. In the ISS method, the scintillator and the substrate are disposed in the reverse order. Note that, a direct conversion type of the detection panel, which has a conversion layer (amorphous selenium or the like) for directly converting X-rays into electric charge, may be used instead.

The pixel 45 is composed of a photodiode 46 and a TFT 47 (switching element). The photodiode 46 is a photoelectric conversion element which produces electric charge (electron and hole pairs) upon entry of visible light.

The photodiode 46 is composed of a semiconductor layer (of a PIN (p-intrinsic-n) type, for example) for producing the electric charge, and upper and lower electrodes disposed on the top and bottom of the semiconductor layer. The lower electrode of the photodiode 46 is connected to the TFT 47. The upper electrode of the photodiode 46 is connected to a bias line 48. The number of the bias lines 48 coincides with the number of rows (n rows) of the pixels 45 arranged on the imaging surface 36. The bias lines 48 are connected to a bus 49. The bus 49 is connected to a bias power source 50. The bias power source 50 applies bias voltage Vb to the upper electrode of every photodiode 46 through the bus 49 and the bias lines 48. The application of the bias voltage Vb produces an electric field in the semiconductor layer. The electric charge (electron and hole pairs) produced in the semiconductor layer by the photoelectric conversion is attracted to the upper and lower electrodes, one of which has positive polarity and the other has negative polarity, then is accumulated in the photodiode 46.

A gate electrode of the TFT 47 is connected to a scan line 51. A source electrode of the TFT 47 is connected to a signal line 52. A drain electrode of the TFT 47 is connected to the photodiode 46. The scan lines 51 and the signal lines 52 are routed into a lattice. The number of the scan lines 51 coincides with the number of the rows (n rows) of the pixels 45 arranged in the imaging surface 36. The number of the signal lines 52 coincides with the number of the columns (m columns) of the pixels 45. Every scan line 51 is connected to a gate driver 53, and every signal line 52 is connected to a signal processing circuit 54.

The circuitry part for controlling drive of the detection panel 35*a* includes a controller 41, a gate driver 53, a signal processing circuit 54 and so on. The controller 41 drives the TFTs 47 through the gate driver 53 so that the detection panel 35*a* carries out the charge accumulation operation in which each pixel 45 accumulates the signal charge in accordance with the amount of X-rays incident thereon, readout operation in which the signal charge is read out from the pixels 45, and the reset operation.

In the charge accumulation operation, while the TFTs 47 are turned off, the pixels 45 accumulate signal charge. In the readout operation, the gate driver 53 sequentially issues gate pulses G1 to Gn each of which drives the TFTs 47 of the same row at a time. Thereby, the scan lines 51 are activated one by one so as to turn on the TFTs 47 connected to the activated scan line 51 on a row-by-row basis. Since the turn-on time is determined by a length of gate pulse, the TFTs 47 return to the off-state after the time determined by the pulse length is passed. Upon turning on of the TFT 47, the signal charge accumulated in the photodiode 46 of the pixel 45 is read out to the signal line 52, and inputted to the signal processing circuit 54.

The signal processing circuit 54 includes integration amplifiers 60, a multiplexer (MUX) 61, an A/D converter (A/D) 62, and so on. The integration amplifier 60 is connected to each signal line 52 on a one-by-one basis. The integration amplifier 60 is composed of an operational amplifier 60*a* and a capacitor 60*b* connected between input and output terminals of the operational amplifier 60*a*. One of the input terminals of the operation amplifier 60*a* is connected to the signal line 52. The other input terminal of the operational amplifier 60*a* is connected to a ground (GND). A reset switch 60*c* is connected in parallel with the capacitor 60*b*. The integration amplifier 60 integrates electric charge input from the signal line 52, and converts the electric charge into each of voltage signals D1 to Dm to be output. The output terminal of every operational amplifier 60*a* is connected to the MUX 61 through an amplifier 63 and a sample holder (S/H) 64. An output of the MUX 61 is connected to the A/D 62.

The MUX 61 sequentially selects one of the plural integration amplifiers 60 connected in parallel, and inputs the voltage signals D1 to Dm output from the selected integration amplifiers 60 in series to the A/D 62. The A/D 62 converts the input voltage signals D1 to Dm into digital data, and outputs the digital data to the memory 42 contained in the electronic cassette 16. An amplifier may be provided between the MUX 61 and the A/D 62.

After the MUX 61 sequentially reads out from the integration amplifiers 60 the voltage signals D1 to Dm of one row, the controller 41 outputs a reset pulse RST to the integration amplifiers 60 to turn on the reset switches 60*c*. Thus, the signal charge of one row accumulated in the capacitors 60*b* is discharged and reset. Upon the reset of the integration amplifiers 60, the gate driver 53 outputs the gate pulse of the next row to start reading out the signal charge from the pixels 45 of the next row. By sequential repetition of this operation, the signal charge is read out from the pixels 45 of every row.

After completion of the readout from every row, the image data representing the X-ray image of one frame is stored in the memory 42. This image data is read out from the memory 42, and output to the console 17 through the communication unit 40. Thereby, the electronic cassette 16 detects the X-ray image of the patient.

Dark charge occurs in the semiconductor layer of the photodiode 46 irrespective of the presence or absence of entry of the X-rays. Due to the application of the bias voltage Vb, the dark charge is accumulated in the photodiode 46 of the pixel 45. The dark charge occurring in the pixels 45 becomes noise of the image data, and therefore the reset operation is carried out to remove the dark charge. The reset operation is an operation in which the dark charge produced in the pixels 45 is discharged through the signal lines 52.

The reset operation adopts for example a sequential reset method by which the pixels 45 are reset on a row-by-row basis. In the sequential reset method, as same as in the readout operation of the signal charge, the gate driver 53 sequentially issues the gate pulses G1 to Gn to the signal lines 51 to turn on the TFTs 47 of the pixels 45 on a row-by-row basis. While the TFT 47 is turned on, the dark charge flows from the pixel 45 through the signal line 52 into the capacitor 60*b* of the integration amplifier 60. In the reset operation, in contrast to the readout operation, the MUX 61 does not read out the electric charge accumulated in the capacitors 60*b*. In synchronization with the issue of each of the gate pulses G1 to Gn, the controller 41 outputs the reset pulse RST. The reset pulse RST turns on the reset switches 60*c*, so the electric charge accumulated in the capacitors 60*b* is discharged, and the integration amplifiers 60 are reset.

Instead of the sequential reset method, a parallel reset method or all pixels reset method may be used. In the parallel reset method, a plurality of rows of pixels are grouped together, and sequential reset is carried out in each group, so as to concurrently discharge the dark charge from the rows of the number of the groups. In the all pixels reset method, the gate pulse is input to every row to discharge the dark charge from every pixel at a time. Adoption of the parallel reset method and the all pixel reset method allows speeding up the reset operation.

Upon receiving the emission start request signal from the controller 21 of the source controller 14, the controller 41 makes the detection panel 35a perform the reset operation, so as to send the emission permission signal back to the source controller 14. After that, upon receiving the emission start signal, the controller 41 makes the detection panel 35a shift from the reset operation to the charge accumulation operation.

The detection panel 35a has, on the single imaging surface 36, not only the normal pixels 45 each connected to the signal line 52 through the TFT 47, but also a plurality of measuring pixels 65 each of which is directly connected to the signal line 52 without through the TFT 47. The measuring pixel 65 functions as a dose measuring sensor that measures X-ray dose applied to the imaging surface 36 through the patient M. In this embodiment, one measuring pixels 65 constitutes one dose measuring sensor. The number of the measuring pixels 65 is about a few percent of the total number of the pixels 45 on the imaging surface 36. The measuring pixel 65 of this embodiment is identical to the pixel 45 about the basic configuration such as the photodiode 46. Accordingly the both can be manufactured by approximately the same manufacturing processes. The measuring pixel 65 has the same size as the pixel 45 has, it is 150 µm×150 µm.

Since the measuring pixel 65 is directly connected to the signal line 52 without through the TFT 47, the signal charge produced in the photodiode 46 of the measuring pixel 65 immediately flows into the signal line 52, regardless of a state of the TFT 47. The measuring pixel 65 continues outputting the signal charge, even if the normal pixels 45 arranged in the same row as the measuring pixel 65 are in the charge accumulation operation. Thus, the electric charge produced in the photodiode 46 of the measuring pixel 65 always flows into the capacitor 60b of the integration amplifier 60 in the signal line 52 connected to the measuring pixel 65. While the detection panel 35a is in the charge accumulation operation, the electric charge accumulated in the capacitor 60b from the measuring pixel 65 is output as voltage value at predetermined sampling intervals, to the A/D 62 through the MUX 61. The A/D converter 62 outputs the voltage value to the memory 42, as dose measuring signal of each of the measuring pixels 65. The dose measuring signal represents dose of X-ray irradiated per unit time. The dose measuring signal being output in predetermined sampling period is output sequentially to the memory 42.

Figure 5:
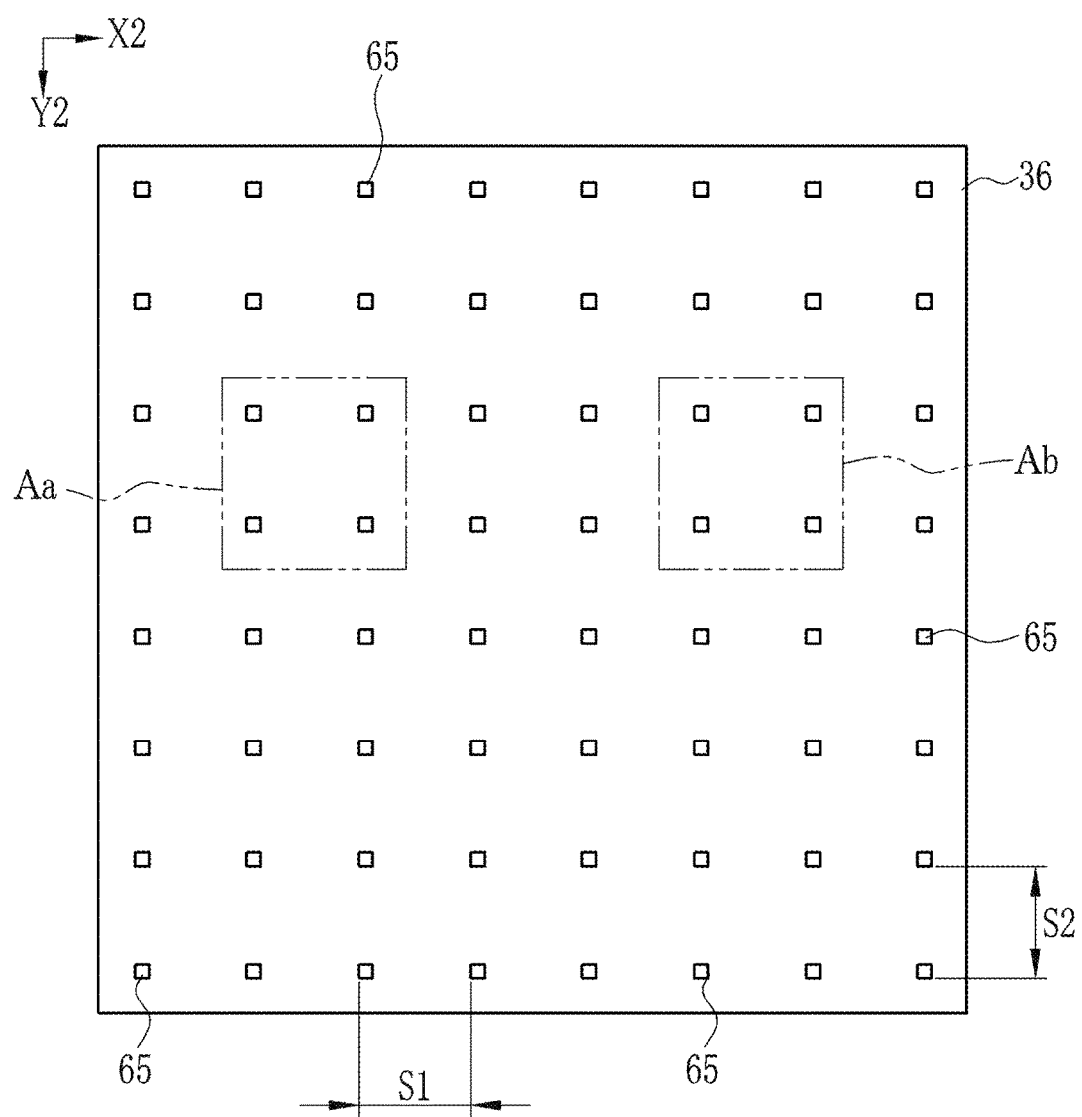
FIG. 5 is an explanatory view of a measuring pixels arrangement and a measurement area of a detection panel of the electronic cassette.

As illustrated in FIG. 5, the measuring pixels 65 are arranged in the X2 direction and the Y2 direction with regular arrangement periods S1 and S2, so as to be uniformly distributed in the imaging surface 36 without being localized. The positions of the measuring pixels 65 are predetermined in manufacturing the detection panel 35a, and a internal memory (not illustrated) of the controller 41 stores in advance the position (coordinates) of every measuring pixel 65 in the imaging surface 36. The dose measuring signal of each of the measuring pixels 65, which the A/D converter 62 outputs, is related to the coordinates information and is recorded in the memory 42.

An AEC section (automatic exposure controller) 67 is controlled by the controller 41. The AEC section 67 reads the dose measuring signal of the each measuring pixel 65 from the memory 42, and performs AEC based on the read dose measuring signal.

Figure 6:
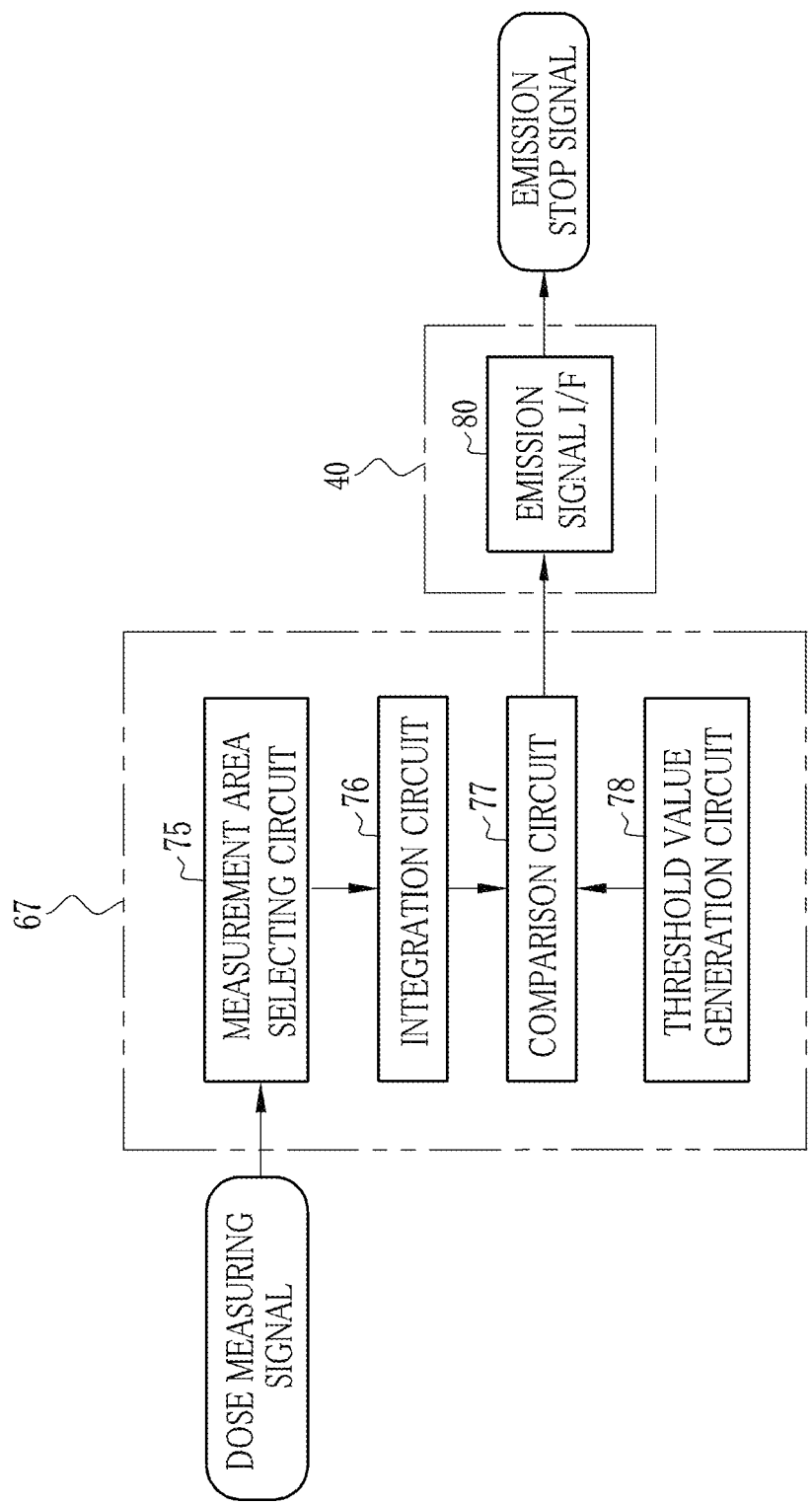
FIG. 6 is a block diagram of an AEC section of the electronic cassette.

As illustrated in FIG. 6, the AEC section 67 has a measurement area selecting circuit 75, an integration circuit 76, a comparison circuit 77, and a threshold value generation circuit 78. The measurement area selecting circuit 75 selects which dose measuring signals from the measuring pixels 65 to be used for the AEC, among the plural measuring pixels 65 arranged all over the imaging surface 36, based on information of the measurement area set depending on the imaging condition. The integration circuit 76 calculates the average value of output values of dose measuring signals from the measuring pixels 65 selected by the measurement area selecting circuit 75. For example, in case areas of symbols Aa and Ab illustrated in FIG. 5 with alternate long and two short dashes lines are selected as the measurement areas, the integration circuit 76 calculates the average value of output values of dose measuring signals of the four measuring pixels 65 for each of the measurement area Aa and the measurement area Ab. Alternatively, the average value of output values of the eight measuring pixels 65 in the measurement area Aa and the measurement area Ab may be calculated. The calculation of the average value is carried out with each sampling of the dose measuring signals. Then the integration circuit 76 integrates the average values to obtain the integrated value. The integrated value represents cumulative dose of irradiated X-ray. The comparison circuit 77 compares the integrated value of the dose measuring signals from the integration circuit 76 with the emission stop threshold value given from the threshold value generation circuit 78. When the integrated value has reached the emission stop threshold value, the comparison circuit 77 outputs the emission stop signal.

The communication unit 40 is connected to an emission signal I/F 80, in addition to the antenna 37 and the socket 39 described above. To the emission signal I/F 80, the emission signal I/F 25 of the source controller 14 is connected. The emission signal I/F 80 performs reception of the emission start request signal, transmission of the emission permission signal in response to the emission start request signal, reception of the emission start signal, and transmission of the emission stop signal which comparison circuit 77 outputs.

Figure 7:
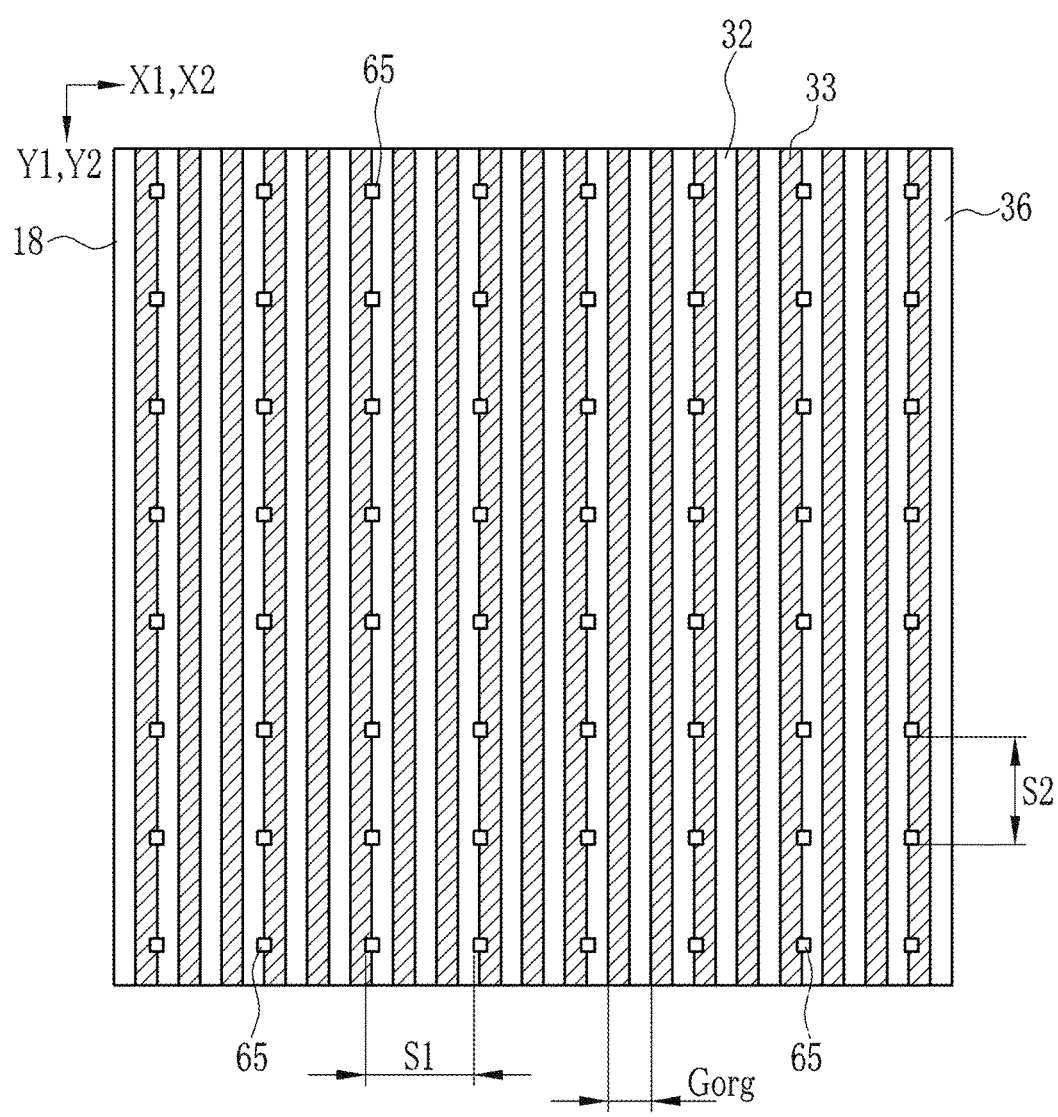
FIG. 7 is an explanatory view of an arrangement state of the measuring pixels when the imaging surface of the detection panel and the grid are overlapped.
Figure 8:
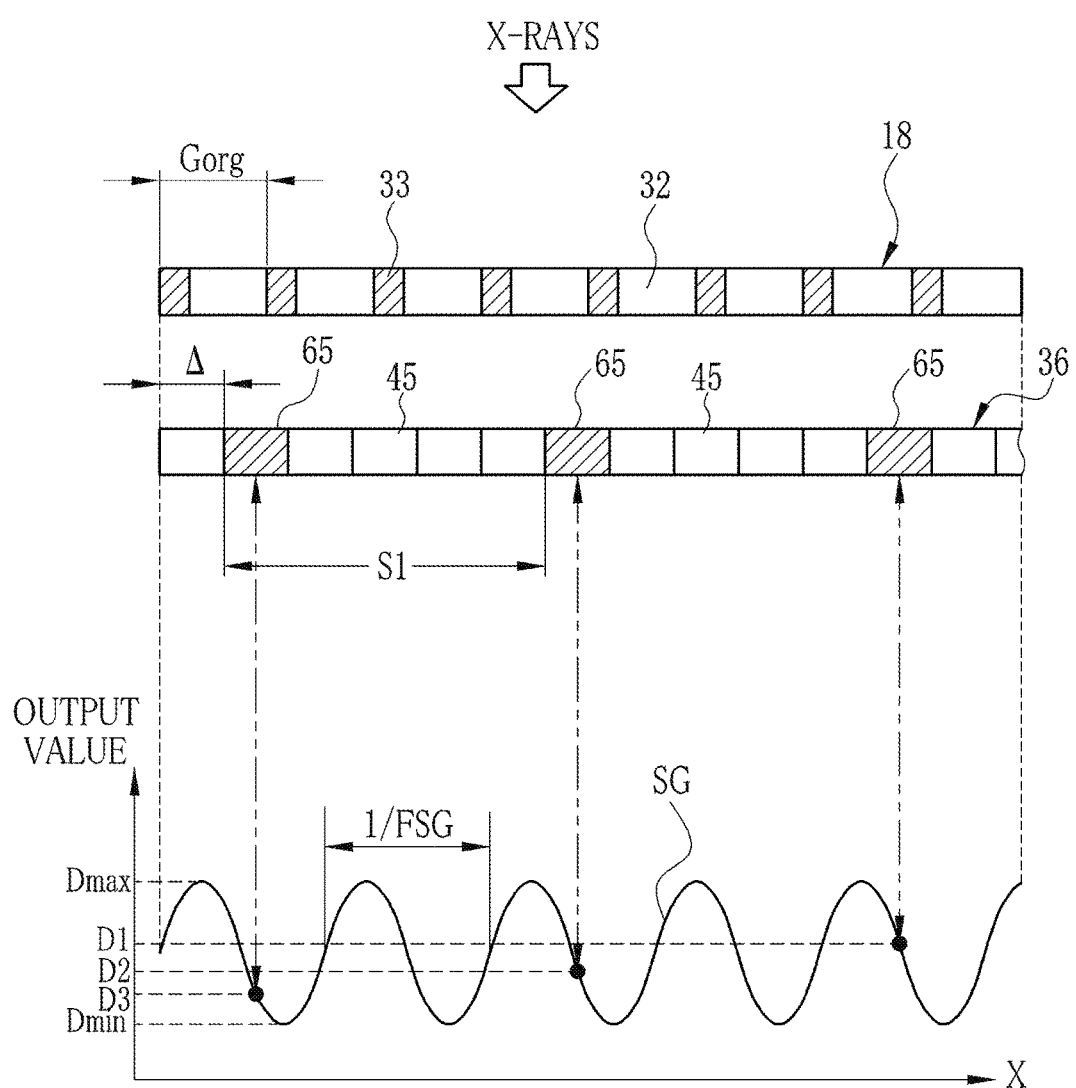
FIG. 8 is an explanatory view of a relation between an arrangement period of the measuring pixels and a fluctuation period of a grid detection signal.
Figure 9:
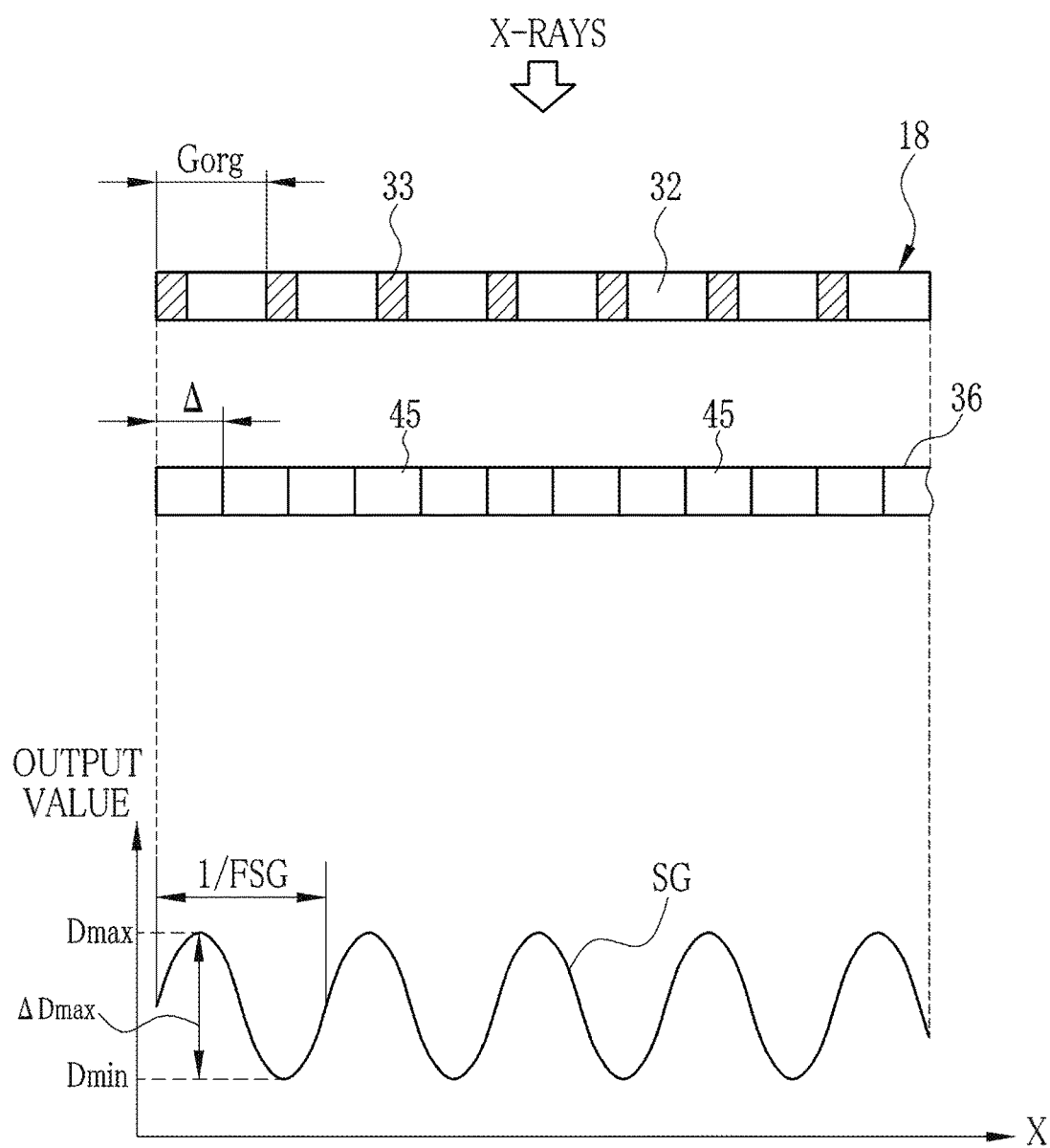
FIG. 9 is an explanatory view of the grid detection signal.

As illustrated in FIG. 7, for performing grid photography using the grid 18, the grid 18 is placed in front (incident side of X-ray) of the imaging surface 36, so that the grid 18 overlaps with the measuring pixels 65. As illustrated in FIG. 8, the arrangement period S1 of the X2 direction of the measuring pixels 65 does not accord with the fluctuation period 1/FSG of output value of grid detection signal SG (S1≠1/FSG), and is not an integral multiple of the fluctuation period 1/FSG. That is, the arrangement period S1≠N(1/FSG): (N is an integer). Note that as illustrated in FIG. 9, the grid detection signal SG is the grid-image signal expressing the image of the grid 18 which is obtained by X-ray being irradiated uniformly on the imaging surface 36 and the detection panel 35a photographing the grid 18.

Even when X-ray is irradiated uniformly on the imaging surface 36, if the grid 18 is placed in front of the imaging surface 36, a part of irradiated X-ray is absorbed in the X-ray absorbing section 33. Accordingly, output values which the pixels 45 on the imaging surface 36 output vary. The grid detection signal SG becomes signal expressing a stripe pattern which reflects the state that the X-ray transmitting sections 32 and the X-ray absorbing sections 33 are in alternative arrangement, and output value of the X2 direction fluctuates periodically between the maximum output value Dmax and the minimum output value Dmin. As the frequency of the grid detection signal SG is expressed as FSG, the fluctuation period of output value becomes 1/FSG which is reciprocal of the frequency FSG.

Since the grid detection signal SG is the image signal expressing the image of the grid 18, if spatial resolution of the detection panel 35a is high enough toward the grid pitch Gorg of the grid 18, the stripe pattern of the grid 18 is reproduced precisely by the grid detection signal SG. Accordingly, the fluctuation period 1/FSG of the grid detection signal SG accords with the grid pitch Gorg.

However, in this embodiment, since the pixel pitch Δ of the pixels 45 is 150 μm and the grid pitch Gorg of the grid 18 is 250 μm, the pixel pitch Δ (150 μm) of the pixels 45 is larger than half (250 μm/2=125 μm) of the grid pitch Gorg (250 μm). Therefore, as fs represents the sampling frequency which expresses the spatial resolution of the detection panel 35a to be determined by the pixel pitch Δ of the pixels 45, the frequency 1/Gorg (1/250 μm) of the grid 18 becomes higher than Nyquist frequency fn (1/(2×150 μm)=1/300 μm) which is ½ of the sampling frequency fs (1/150 μm). In case of such a combination of the detection panel 35a and the grid 18, when the grid 18 is photographed by the detection panel 35a, folding noise is caused in the grid detection signal SG by Nyquist theorem. When folding noise occurs, the grid detection signal SG cannot reproduce the image of the grid 18 precisely, and the grid pitch Gorg does not accord with the fluctuation period 1/FSG of the grid detection signal.

Specifically, the sampling frequency fs of the detection panel 35a is 1/150 μm=0.0067/μm (6.7/mm), and the Nyquist frequency fn is 1/(2×150 μm)=0.0033/μm (3.3/mm). Since the grid density of the grid 18 is 40 lines/cm (4 lines/mm), the frequency FSG of the grid detection signal SG is folded at the Nyquist frequency fn and becomes 3.3−(4−3.3)=2.6/mm. The fluctuation period 1/FSG becomes 1/(2.6/mm)=0.384 mm (384 μm) and does not accord with the grid pitch Gorg=250 μm. Output of the grid detection signal SG fluctuates in the fluctuation period 1/FSG=0.384 mm (384 μm) in the X2 direction. In addition, the grid detection signal SG is simplified in the drawings as a serial signal. However, in reality, since the grid detection signal SG is composed of the output values of the pixels 45, it becomes discrete value according to the sampling frequency fs.

The measuring pixels 65 are placed based on such the grid detection signal SG, so that the arrangement period S1 of the measuring pixels 65 does not accord with the fluctuation period 1/FSG of the grid detection signal SG. Wherein the arrangement period S1 is the length based on the number of the pixels 45. In this example, as illustrated in FIG. 8, the measuring pixels 65 are placed every four pixels, in other words, the four pixels 45 are placed between the two measuring pixels 65. In case that the measuring pixels 65 are placed every four pixels, the arrangement period S1 of the measuring pixels 65 becomes the total number that one measuring pixel 65 is added to the number of pixels 45 placed between the two measuring pixels 65, which is 4+1=5. In this example, the fluctuation period 1/FSG of the grid detection signal SG is 384 μm, and by being converted into the number of the pixels 45, it becomes 384 μm/150 μm=2.56. Accordingly, the converted number (2.56) by the conversion of the fluctuation period 1/FSG (384 μm) of the grid detection signal SG into the number of the pixels 45 does not accord with the arrangement period S1(5) of the measuring pixels 65. In addition, it becomes 5/2.56=1.95 when the arrangement period S1(5) is divided by the converted number (2.56) of the fluctuation period 1/FSG. Accordingly, the arrangement period S1 is not an integral multiple of the fluctuation period 1/FSG of the grid detection signal SG.

As described above, since the arrangement period S1≠N (1/FSG): (N is an integer), it never occurs that all of the plural measuring pixels 65 are placed at the position of the maximum output value Dmax or the place of the minimum output value Dmin of the grid detection signal SG. In other words, it never occurs that output values of all the measuring pixels 65 become the maximum output value Dmax or the minimum output value Dmin.

Figure 10:
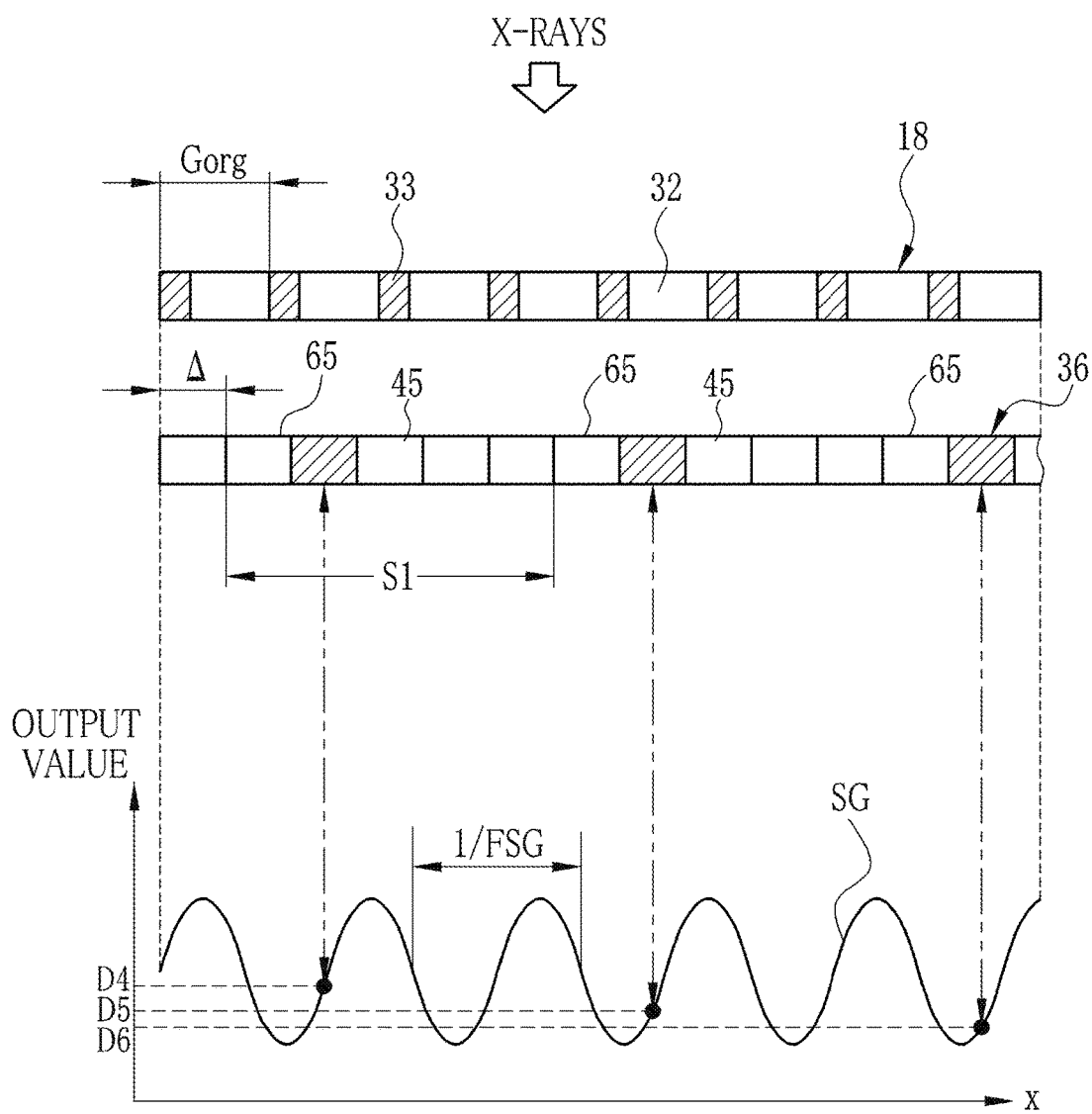
FIG. 10 is an explanatory view of a change in output value of the detection signal when it is shifted for one pixel from the state in FIG. 8.

In an example illustrated in FIG. 8, the output values of dose measuring signals of the measuring pixels 65 are D1 to D3, and disperse in a range between the maximum output value Dmax and the minimum output value Dmin. And as illustrated in FIG. 10, if the geometric layout of the grid 18 and the measuring pixels 65 deviates from the state illustrated in FIG. 8 for a length of one pixel 45 due to production errors and installation backlash of the grid 18, the output values of dose measuring signals of the measuring pixels 65 become D4 to D6, and disperse in a range between the maximum output value Dmax and the minimum output value Dmin. Also in this case, it never occurs that output values of all the measuring pixels 65 become the maximum output value Dmax or the minimum output value Dmin.

The output values of the plurality of measuring pixels 65 disperse in a range between the maximum output value Dmax and the minimum output value Dmin. Accordingly a fluctuation range of the average of the output values becomes smaller than the maximum output difference ΔDmax, which is the difference between the maximum output value Dmax and the minimum output value Dmin. As described above, the AEC section 67 uses the average value of the output values of the measuring pixels 65 in the measurement area Aa and the measurement area Ab illustrated in FIG. 5, for judgment of AEC. When a fluctuation range of an average value becomes small, even if the geometric layout of the measuring pixels 65 and the grid 18 shifts, an output value depending on dose to be incident on the measurement areas Aa and Ab becomes stable. Accordingly, a stable AEC which is not affected by the shift of geometric layout of the grid 18 and the measuring pixels 65 can be performed.

Figure 11:
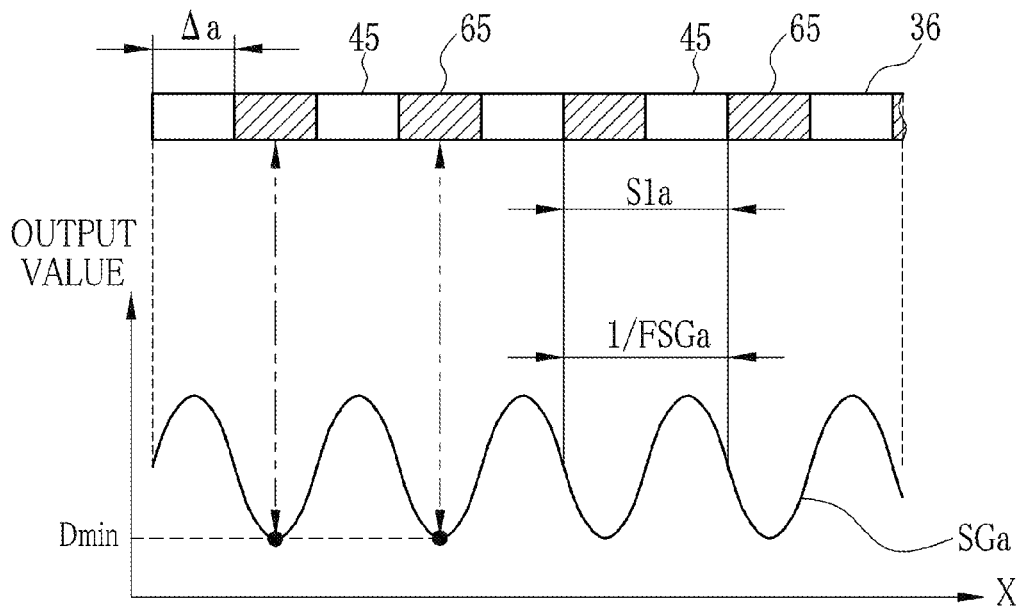
FIG. 11 is an explanatory view of a first comparison example.
Figure 12:
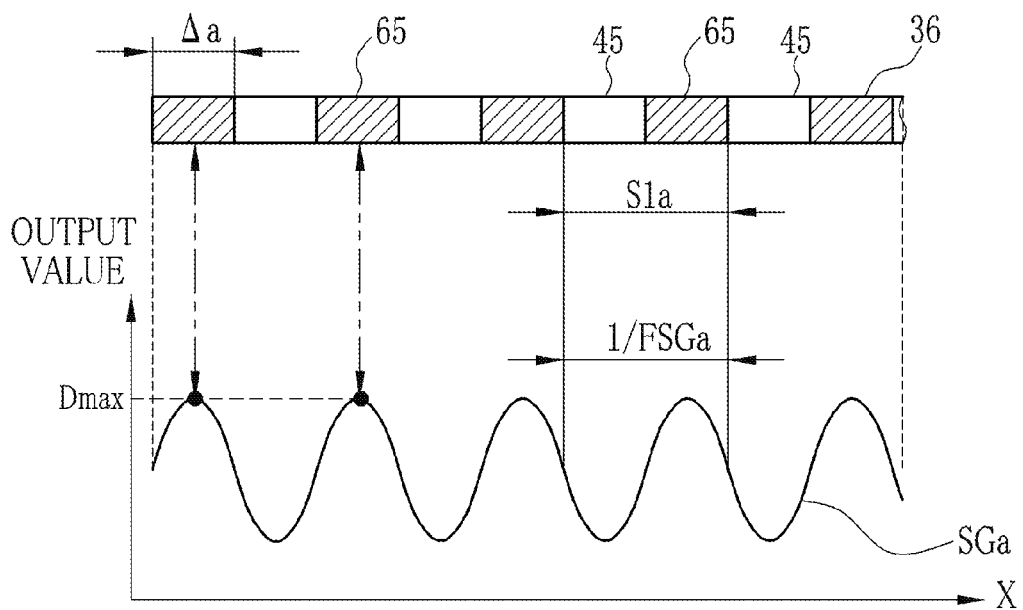
FIG. 12 is an explanatory view of the first comparison example when it is shifted for one pixel from the state in FIG. 11.

In contrast, like comparison examples illustrated in FIG. 11 and FIG. 12, when it becomes an arrangement period S1a=a fluctuation period 1/FSGa, the fluctuation range of output values of the measuring pixels 65 becomes the maximum output difference ΔDmax. In FIGS. 11 and 12, the symbol Δa represents the pixel pitch of the pixels 45. The measuring pixels 65 are placed every other pixel, the arrangement period S1a of the measuring pixels 65 is the length for the two pixels 45. The symbols SGa, FSGa respectively represents the grid detection signal and a frequency of the grid detection signal in the comparison example.

In case the arrangement period S1a=the fluctuation period 1/FSGa, output values of the measuring pixels 65 become the same and do not vary. And depending on a geometric layout of the grid 18 and the measuring pixels 65, there become possible the cases that the output value of each of the measuring pixels 65 becomes the minimum output value Dmin as illustrated in FIG. 11, and that the output value of each of the measuring pixels 65 becomes the maximum output value Dmax as illustrated in FIG. 12. In the comparison example, since an output value of each of the measuring pixels 65 becomes the same, the average of the output values of the measuring pixels 65 becomes the same as the output value of the one measuring pixel 65. Accordingly, a fluctuation range of the average value becomes the maximum output difference ΔDmax, which is the difference between the maximum output value Dmax and the minimum output value Dmin. When the fluctuation range of the average value becomes large, influence of a shift of geometric layout of the grid 18 and the measuring pixels 65 becomes greater. Accordingly, a stable AEC cannot be performed.

Figure 13:
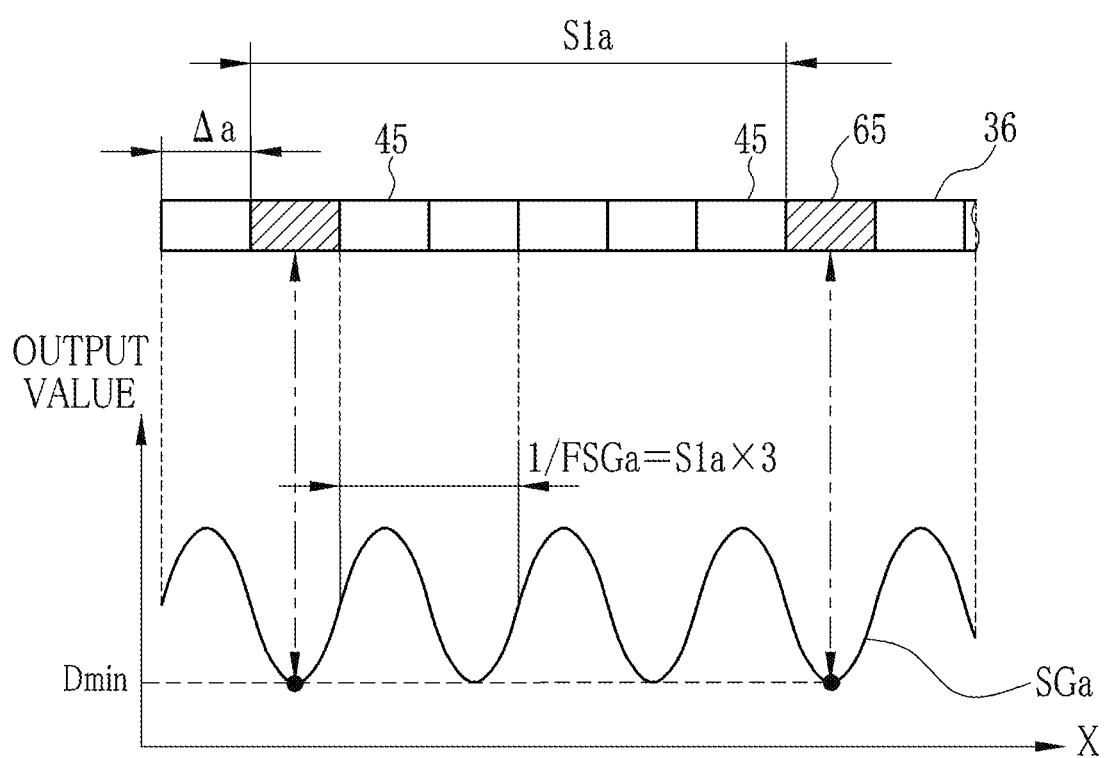
FIG. 13 is an explanatory view of a second comparison example.

In a comparison example illustrated in FIG. 13, the arrangement period S1a illustrated in FIGS. 11 and 12 becomes three times as long as the fluctuation period 1/FSG. Also in case that the arrangement period S1a becomes the integral multiple of the fluctuation period 1/FSG in this way, output values of the plural measuring pixels 65 become the same, like the cases in FIGS. 11 and 12. Therefore, like the comparison examples illustrated in FIGS. 11 and 12, the fluctuation range of output values of the measuring pixels 65 becomes the maximum output difference ΔDmax. Accordingly, a stable AEC cannot be performed.

As described above, the fluctuation period 1/FSG of the grid detection signal SG may be calculated based on the sampling frequency Fs of the detection panel 35a determined by the pixel pitch Δ of the pixels 45 and the grid pitch Gorg. Or the frequency FSG of the grid detection signal SG and the fluctuation period 1/FSG may be calculated by obtaining the grid detection signal SG through actual photography of the grid 18 with use of the detection panel 35a and applying Fourier transform or the like to the obtained grid detection signal SG. Photography and calculation to obtain the grid detection signal SG are carried out at the time of a design or a production of the electronic cassette 16. And the arrangement periods S1, S2 are determined based on the acquired fluctuation period 1/FSG of the grid detection signal SG. In case that several kinds of the grid 18 varying in grid density are used in combination with one electronic cassette 16, the grid detection signal SG is obtained for each kind of the grid 18. Then based on the plurality of obtained grid detection signals SG, the arrangement period S1 is determined to meet the condition, the arrangement period S1≠N(1/FSG): (N is an integer).

Figure 14:
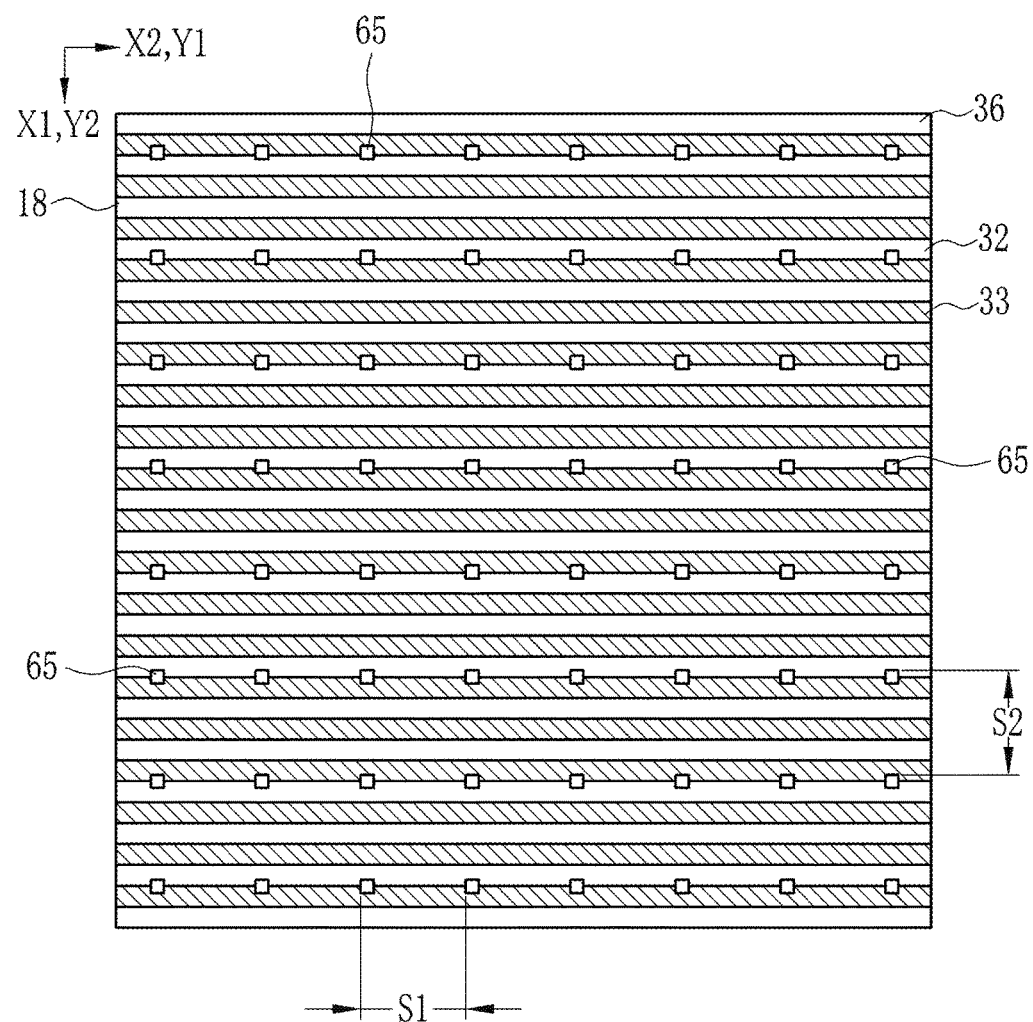
FIG. 14 is an explanatory view of an arrangement state of the measuring pixels when the imaging surface of the detection panel and the grid are overlapped with rotating the grid 90 degrees.

In addition, the pixel 45 is a square pixel, and the pixel pitch of the pixels 45 in the Y2 direction is A, as same as in the X2 direction. And the arrangement period S2 of the measuring pixels 65 in the Y2 direction becomes the same as the arrangement period S1. Accordingly, the arrangement period S2 does not accord with the fluctuation period 1/FSG of the grid detection signal SG, and is not an integral multiple of the fluctuation period 1/FSG. That is, regarding the arrangement period S2, like the arrangement period S1, there is the relation that the arrangement period S2≠1/FSG (the arrangement period S2≠N(1/FSG): (N is an integer)). Therefore, as illustrated in FIG. 14, even when the grid 18 is used in a state turned 90 degrees from the state illustrated in FIG. 7, a fluctuation range of the average of the output values from the plurality of measuring pixels 65 becomes smaller than the maximum output difference ΔDmax. Accordingly, a stable AEC can be performed.

Figure 15:
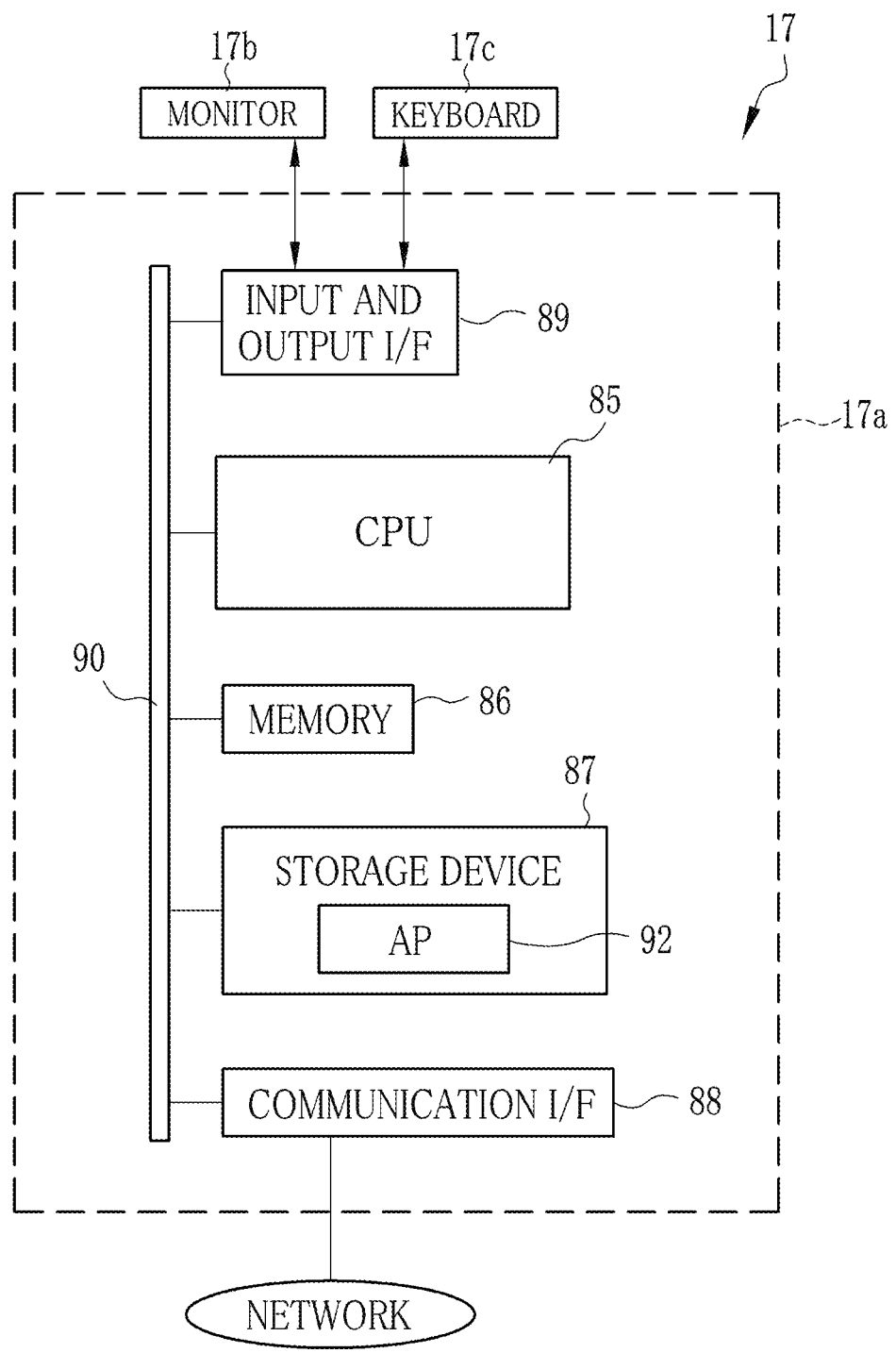
FIG. 15 is a block diagram of a console.

As illustrated in FIG. 15, the console 17 includes a console main unit 17a, a monitor 17b and a keyboard 17c. The console 17 is communicably connected to the electronic cassette 16 in a wired or wireless method, to control the operation of the electronic cassette 16. To be more specific, the console 17 transmits the imaging condition to the electronic cassette 16 to set up a AEC condition and a signal processing condition (e.g. gain of an amplifier for multiplying voltage corresponding to the accumulated signal charge) of the signal processing circuit 54. Additionally, the console 17 controls the operation of the electronic cassette 16, more specifically, powers on and off the electronic cassette 16, and performs mode switching into a power saving mode, an imaging preparation mode, and the like.

The console 17 applies various types of image processes such as offset correction, gain correction, and defect correction to the X-ray image data transmitted from the electronic cassette 16. In the defect correction, pixel values of the row having the measuring pixel 65 are interpolated using the pixel values of the adjacent row without having the measuring pixel 65. The X-ray image after being subjected to the image processes is displayed on a monitor 17b. The X-ray image data is written to a storage device 87 and a memory 86 in the console main unit 17a, or an image storage server connected to the console 17 through a network. Note that the various image processes mentioned above may be executed in the electronic cassette 16.

The console 17 receives an input of an examination order, which includes information about the sex and age of the patient, the body part to be imaged, and the purpose of imaging, and displays the examination order on the monitor 17b. The examination order is input from an external system e.g. HIS (hospital information system) or RIS (radiography information system) that manages patient data and examination data related to radiography, or inputted manually by the operator. The examination order includes the body part to be imaged e.g. head, chest, abdomen or the like, and an imaging direction e.g. anterior, medial, diagonal, PA (X-rays are applied from a posterior direction), or AP (X-rays are applied from an anterior direction). The operator confirms the contents of the examination order on the monitor 17b, and inputs the imaging condition corresponding to the contents through an operation screen of the console 17.

As illustrated in FIG. 16, the imaging condition for each body part can be set in the console 17. The imaging condition includes the tube voltage, the tube current, the measurement area of the measuring pixels 65, the emission stop threshold value used for comparison with the integrated value of the AEC measurement signals to judge the stop of the X-ray emission, and the like. The information about the imaging condition is stored in the storage device 87. An operator refers to the imaging condition of the console 17, and manually sets the same condition as the imaging condition of the source controller 14.

The measurement area represents an area of the measuring pixels 65 to be used for an AEC. The area set as the measurement area is an area corresponding to an area of interest, which is the most notable area at the time of diagnosis for each body part, and where the dose measuring signal can be obtained stably. For example, when a chest is photographed, as illustrated with the measurement areas Aa, Ab surrounded with dotted lines in FIG. 5, the areas corresponding to the lung field are set as the measurement areas. The measurement area is represented by X and Y coordinates. When the first measurement area is in a rectangular shape, as in the case of this embodiment, for example, the X and Y coordinates of two corner points connected by a diagonal line are stored. The X and Y coordinates correspond to the position of the pixels 45 (including the measuring pixels 65) in the imaging surface 36 of the electronic cassette 16. An X axis extends in a direction parallel to the scan lines 51, and a Y axis extends in a direction parallel to the signal lines 52. The coordinates of the pixel 45 at the upper left corner are assigned as the origin point (0, 0).

As illustrated in FIG. 15, the console main unit 17a is composed of a CPU 85, the memory 86, the storage device 87, a communication I/F 88, and an input and output I/F 89. These components are connected to each other via a data bus 90. The monitor 17b and the keyboard 17c are connected to the console main unit 17a through the input and output I/F 89. Note that replacing with the keyboard 17c, a mouse or a touch panel may be used.

The storage device 87 is a hard disk drive (HDD), for example. The storage device 87 stores control programs and application programs (hereinafter referred as the AP) 92. The AP 92 makes the console 17 perform various functions related to the X-ray imaging, such as a display process of the examination order and the X-ray image, the image process of the X-ray image, and a setup of the imaging condition.

The memory 86 is a work memory used for processing of the CPU 85. The CPU 86 loads the control programs stored on the storage device 87 into the memory 86, and runs the programs for overall control of the computer. The communication I/F 88 functions as a network interface for performing wireless or wired transmission control from/to an external device such as the RIS, the HIS, the image storage server, and the electronic cassette 16.

Figure 17:
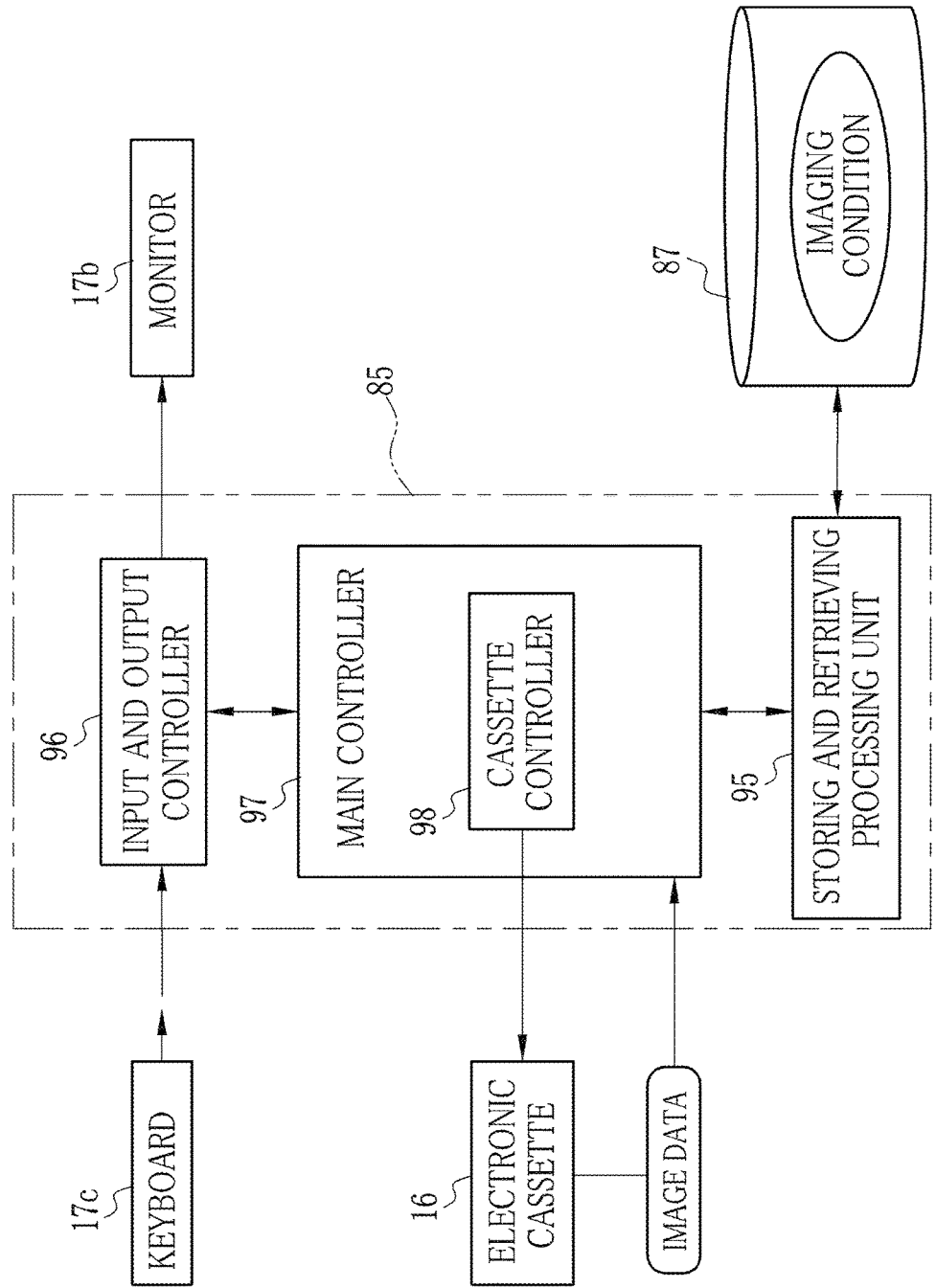
FIG. 17 is a block diagram showing the function and the information flow of the console.

As illustrated in FIG. 17, by running the AP 92, the CPU 85 of the console 17 functions as a storing and retrieving processing unit 95, an input and output controller 96, and a main controller 97. The storing and retrieving processing unit 95 stores various types of data to the storage device 87, and retrieves the data from the storage device 87. The input and output controller 96 reads out drawing data from the storage device 87 in accordance with the operation of the keyboard 17c, and outputs to the monitor 17b various types of operation screens of GUIs based on the read drawing data. The input and output controller 96 receives an input of an operation command from the keyboard 17c through the operation screen. The main controller 97 performs overall control of the console 17. Also, the main controller 97 has a cassette controller 98 that controls the operation of the electronic cassette 16. The cassette controller 98 receives the information of the measurement area according to the set imaging condition and the information of the emission stop threshold value, from the storing and retrieving processing unit 95. The cassette controller 98 provides the received information to the electronic cassette 16.

Further, in the console 17, the CPU 85 establishes an image processor for applying various types of image processes such as the offset correction, the gain correction, and the defect correction to the image data, and a communication unit for mediating communication with the source controller 14 and the electronic cassette 16. The function of each component may be embodied by hardware instead of software. Note that all or part of the image processes such as the offset correction, the gain correction, and the defect correction may be executed in the electronic cassette 16.

Figure 18:
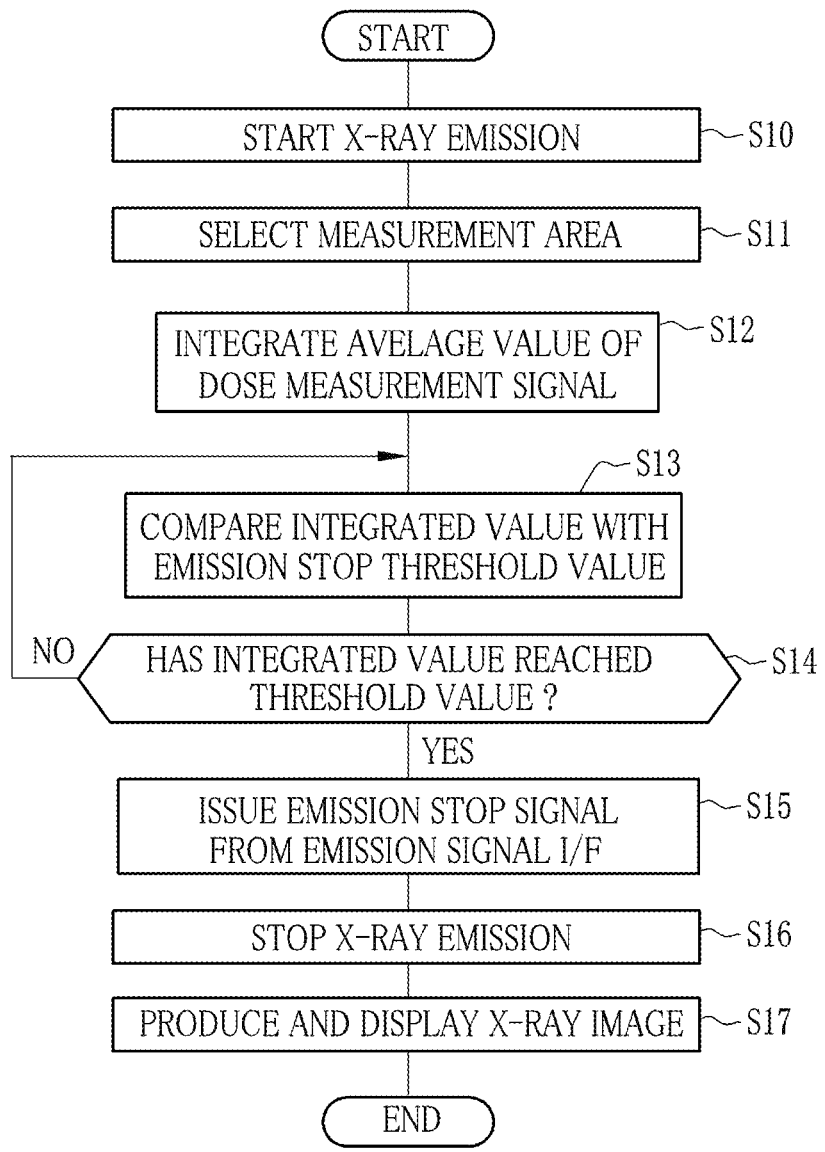
FIG. 18 is a flowchart of procedures of an X-ray photography.

Next, the operation of the X-ray imaging system 10 will be described with referring to a flowchart of FIG. 18.

Firstly, while the patient M stands in a predetermined position in front of the imaging stand 30, the height and the horizontal position of the electronic cassette 16 loaded in the imaging stand 30 are adjusted to align the electronic cassette 16 with the patient's body part to be imaged. In accordance with the position of the electronic cassette 16 and the size of the body part, the height and horizontal position of the X-ray source 13 and the size of the irradiation field are adjusted.

Then, the electronic cassette 16 is turned on. The operator enters the imaging condition and the mode setting information from the keyboard 17c to the electronic cassette 16. Thus, the cassette controller 98 sets to the electronic cassette 16 the imaging condition and the information of the measurement area, the emission stop threshold value, and the like corresponding to the imaging condition. The imaging condition is also set to the source controller 14.

After completion of imaging preparation, the emission switch 15 is half-pressed by the operator. Thereby, the warm-up start signal is transmitted to the source controller 14, so the X-ray source 13 starts warming up. After a lapse of predetermined time, the emission switch 15 is full-pressed, and the emission start signal is transmitted to the source controller 14. Thus, the X-ray emission is started (S10). X-ray irradiated by the X-ray source 13 produces scattered radiation when penetrating the patient M. However, this scattered radiation is removed by the grid 18.

Before the start of the X-ray emission, the detection panel 35a repeats the reset operation. Upon receiving the emission start signal from the source controller 14, the detection panel 35a shifts from the reset operation to the charge accumulation operation.

At the same time as the start of the charge accumulation operation of the detection panel 35a, the AEC section 67 starts the AEC based on the dose measuring signal from the measuring pixels 65. The measurement area selecting circuit 75 selects dose measuring signals from the measuring pixels 65 in the measurement area, among dose measuring signals of the plurality of measuring pixels 65 input by the A/D converter 62, based on information of the measurement area given from the console 17. The selected dose measuring signals are output to the integration circuit 76 (S11). The integration circuit 76 integrates an average value of the output value of the dose measurement signals (S12).

Since the relationship between the arrangement period S1 of the X2 direction and the arrangement period S2 of the Y2 direction of the measuring pixels 65 and the fluctuation period 1/FSG of the grid detection signal SG is that the arrangement periods S1, S2≠N(1/FSG): (N is an integer), the output values of the plurality of measuring pixels 65 disperse. Therefore, even if the geometric layout of grid 18 and measuring pixels 65 shifts, there becomes a small fluctuation range of average of output value of the measuring pixels 65. Accordingly, a stable AEC which is not affected by the shift of geometric layout of the grid 18 and the measuring pixels 65 can be performed.

The threshold value generation circuit 78 generates the emission stop threshold value provided by the cassette controller 98, and outputs the emission stop threshold value to the comparison circuit 77. The comparison circuit 77 compares the integrated value of the dose measuring signals with the emission stop threshold value (S13). When the integrated value has reached the emission stop threshold value (YES in S14), the emission stop signal is outputted. The emission stop signal is transmitted to the emission signal I/F 25 of the source controller 14 through the emission signal I/F 80 (S15).

Upon receiving the emission stop signal by the source controller 14, the controller 21 stops the electric power supply from the high voltage generator 20 to the X-ray source 13, and therefore the X-ray emission is stopped (S16). When an emission stop detection circuit of the AEC section 67 detects the stop of the X-ray emission, the detection panel 35a stops the charge accumulation operation and shifts to the readout operation. Thereby the X-ray image is output to the memory 42. After the readout operation, the detection panel 35a restarts the reset operation.

The X-ray image is transmitted to the console 17 through the communication unit 40. The X-ray image is subjected to the various types of image processes and then displayed on the monitor 17b through the input and output controller 96 (S17).

The present invention makes a fluctuation range of output values of the measuring pixels 65 small by determining the arrangement periods S1 and S2 of the measuring pixels 65 based on the relationship between the grid detection signal SG and the fluctuation period 1/FSG. Therefore, there is no need to obtain a gain image for each photography so as to correct an output value of each of the measuring pixels based on the obtained gain image, not like the U.S. Pat. No. 6,944,266. Furthermore, in the U.S. Pat. No. 6,944,266, appropriate correction of an output value is not possible when the geometric layout of the grid 18 and the measuring pixels 65 shifts by a shock or so on after having obtained a gain image. Accordingly, an AEC cannot be performed appropriately. However, the present invention can perform an appropriate AEC even if the geometric layout shifts.

In addition, in the above embodiment, since one dose measuring sensor is constituted of one measuring pixel 65 having the same size as the pixel 45, a density step highly visible by human eye does not occur in an X-ray image, not like the U.S. Pat. No. 6,952,465 which provides dose measuring sensors of a stripe shape with the length for 500 pixels. Accordingly, there is little concern about picture quality deterioration of X-ray image. In addition, the defect correction is easy to be executed because the size of the measuring pixel 65 is small.

In this way, the measuring pixels 65 are handled as defect pixels, and a defect correction for interpolation using pixel values of the peripheral pixels 45 is performed. In the defect correction, since the correction precision becomes high as the size of the measuring pixels 65 is smaller, smaller size of the measuring pixel 65 is more preferable in view of the picture quality. On the other hand, it becomes more easily influenced by a position of the X-ray absorbing section 33 of the grid 18, as the size of the measuring pixels 65 is smaller. In other words, regarding the single measuring pixel 65, there becomes a demerit that a fluctuation range of output values becomes larger by a shift of the geometric layout with the grid 18. However, in the present invention, since the arrangement period S1 is different from the fluctuation period 1/FSG of the grid detection signal SG, output values of the plurality of measuring pixels 65 can disperse. In addition, it never occurs that output values of all the measuring pixels 65 become the maximum output value Dmax or the minimum output value Dmin. And since output values of the plurality of the measuring pixels 65 are averaged, the stable AEC can be performed even if a fluctuation range of each output value grows larger by reducing size of the each measuring pixel 65.

Furthermore, since the measuring pixels 65 are arranged in a periodic manner, an algorithm of the defect correction is easy to be simplified in comparison with the case that they are not arranged periodically. In addition, forming of the measuring pixels 65 at the time of the manufacture is easy. Therefore there is a merit that the manufacture cost can be reduced.

In addition, the arrangement periods S1 and S2 which are in the X2 direction and Y2 direction of the measuring pixels 65 are the same, and the relation between the arrangement periods S1, S2 and the fluctuation period 1/FSG of the grid detection signal SG is that the arrangement periods S1, S2≠N(1/FSG): (N is an integer). Accordingly, a stable AEC can be performed both in the position that the arrangement direction X1 of the grid 18 accords with the X2 direction of the imaging surface 36 and in the position that the arrangement direction X1 accords with the Y2 direction of the imaging surface 36.

In addition, in case that the plane geometry is four-square, like the electronic cassette 16 of this embodiment, at a glance it is hard to be confirmed whether that the X2 direction is parallel to the horizontal direction (the longitudinal position) or that the Y2 direction is parallel to the horizontal direction (the lateral position). In case that the dose measuring sensors of a stripe shape described in the U.S. Pat. No. 6,952,465 is applied to the square-shaped electronic cassette 16 and the grid 18, there becomes inconvenient because it must be carefully confirmed that the direction of the stripe of the dose measuring sensors is non-parallel to the direction of the stripe of the grid 18. Furthermore, the confirmation of the posture is not possible in a condition that the electronic cassette 16 is set in the holder 30a. Accordingly there becomes more inconvenient because the electronic cassette 16 must be removed from the holder 30a. In this respect, in this embodiment, the arrangement periods S1 and S2 which are in the X2 direction and Y2 direction of the measuring pixels 65 do not accord with the fluctuation period 1/FSG of the grid detection signal SG. Accordingly, it is not necessary to confirm postures of the electronic cassette 16 and the grid 18 carefully, and this contributes high convenience.

Note that the arrangement periods S1 and S2 of the measuring pixels 65 are not necessary to be the same. Only if each of the arrangement period S1 and the arrangement period S2 is different from the fluctuation period 1/FSG of the grid detection signal SG, a fluctuation range of the average value of the measuring pixels 65 becomes small and an stable AEC can be performed.

However, it is more preferable that the arrangement period S2 and the arrangement period S1are the same. Whether a stable AEC can be performed is determined by a relationship between the arrangement periods S1, S2 and the fluctuation period 1/FSG of the grid detection signal SG. In some kinds (grid density) of the grid 18, since the arrangement periods S1 and S2 accord with the fluctuation period 1/FSG of the grid detection signal SG, a stable AEC cannot be performed. Therefore, for performing grid photography with the electronic cassette 16, it is necessary to examine each kind of the grid 18 whether it is possible to perform the stable AEC in combination with the electronic cassette 16. Such the examination work is performed based on a grid density of the arrangement periods S1, S2 and the grid 18. If the arrangement periods S1 and S2 accord with each other, it increases convenience because it is only necessary to examine one of the arrangement periods S1 and S2. In addition, if the arrangement periods S1 and S2 are different, since even with the same grid 18, there are both a case it is possible to perform a stable AEC and a case it is not possible, depending on a posture of the electronic cassette 16, there becomes less convenient in comparison with the case that the arrangement periods S1 are S2 the same.

In addition, if the arrangement periods S1 and S2 are different, the number of the measuring pixels 65 included in the measurement areas Aa and Ab of the same size may be different depending on longitudinal and lateral positions of the electronic cassette 16. In such a case, it is necessary to change an algorithm for calculating integrated value using the measuring pixels 65 and so on, according to the direction. If the arrangement periods S1 and S2 are the same, since the number of the measuring pixels 65 included in the measurement areas of the same size become the same, the algorithm can be commonized. From above reasons, it is preferable that the arrangement periods S1 and S2 are the same.

In the above embodiment, the electronic cassette 16 and the grid 18 whose plane geometry is four-square are used, however, an electronic cassette and a grid whose plane geometry is rectangle may be used. As the electronic cassette whose plane geometry is rectangle, for example, there is one having a size in conformity with the international standard ISO4090:2001, which is the same standard for a film cassette and an IP (imaging plate) cassette.

Also in case of using the electronic cassette whose plane geometry is rectangle, it is preferable that the arrangement periods S1 and S2 are the same. In case of using the rectangular electronic cassette, when a chest of a patient of a standard figure is photographed, the electronic cassette is placed so that the longitudinal direction of the electronic cassette goes along the height direction of the patient. And when a chest of a patient fatter than normal is photographed, the electronic cassette may be turned 90 degrees so that the longitudinal direction of the electronic cassette goes along the width direction of the patient body. When the dose measuring sensors of the stripe shape of the U.S. Pat. No. 6,952,465 are used for such the rectangular electronic cassette, even if the direction of the stripes of the grid is at right angle to the direction of the stripes of the dose measuring sensors in the photography of the standard figure patient, the direction of the stripe of the grid accords with the direction of the stripe of the dose measuring sensors when the electronic cassette is turned 90 degrees. However, in this embodiment, since the arrangement periods S1 and S2 which are in the X2 direction and Y2 direction of the measuring pixels 65 do not accord with the fluctuation period 1/FSG of the grid detection signal SG, this problem does not occur.

Second Embodiment

Figure 19:
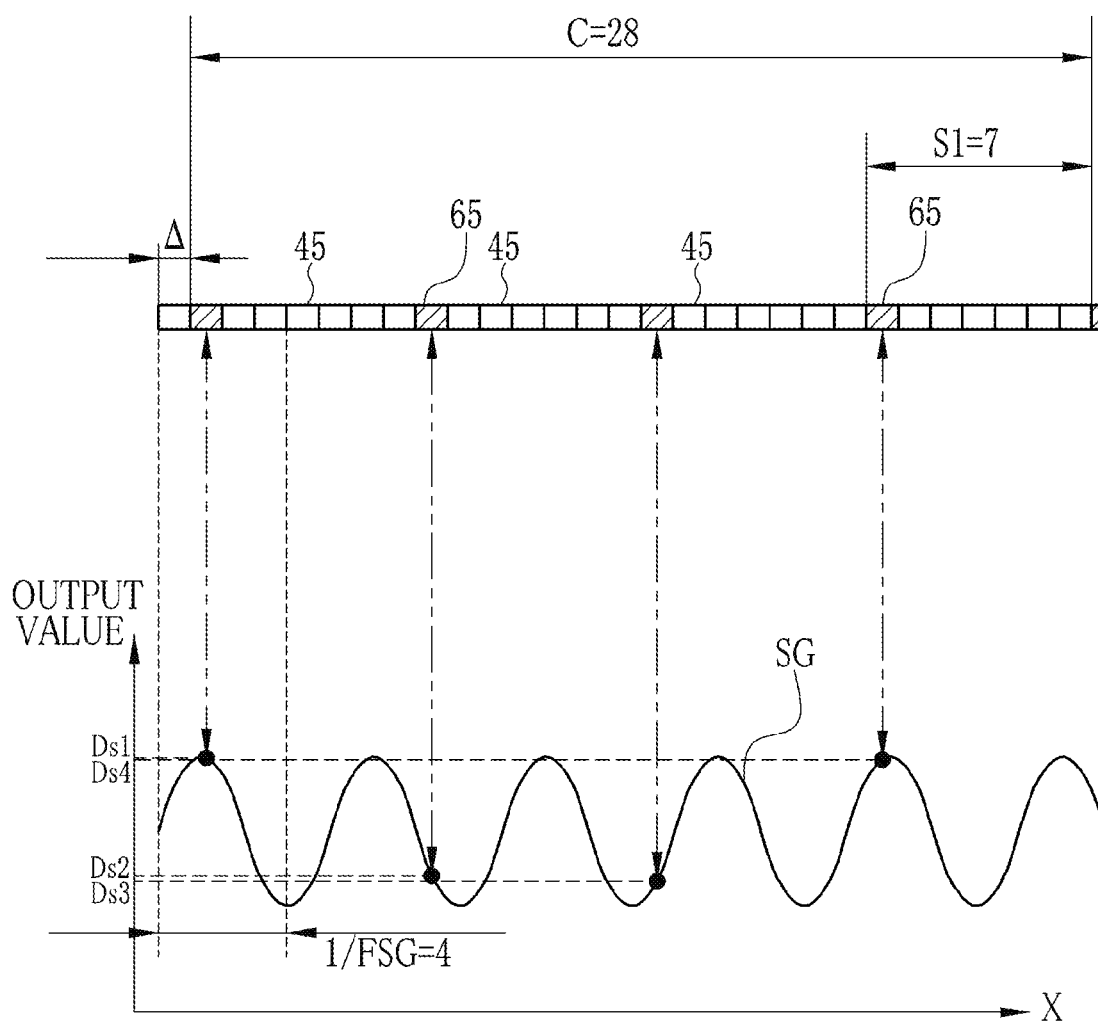
FIG. 19 is an explanatory view of a first example of a second embodiment.

In FIG. 19, the arrangement period S1 becomes seven, because an interval corresponding to the six pixels 45 is provided between the two measuring pixels 65. The converted number by the conversion of the fluctuation period 1/FSG of the grid detection signal SG into the number of the pixels 45 becomes four, because it has a length corresponding to the four pixels 45. Similarly, in an example illustrated in FIG. 20, the arrangement period S1 is six, and the fluctuation period 1/FSG is four.

Figure 20:
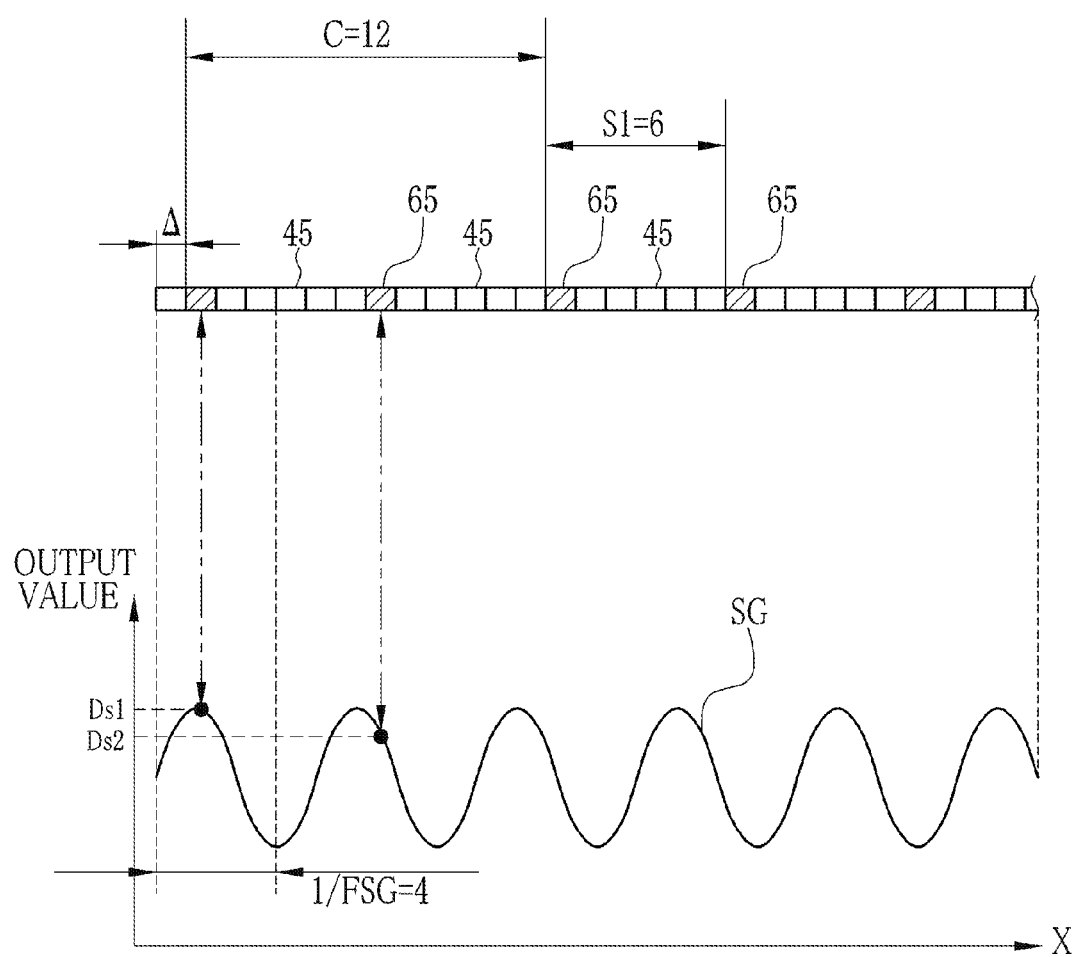
FIG. 20 is an explanatory view of a second example of the second embodiment.

Both of FIG. 19 and FIG. 20 are the embodiments included in the present invention, because they satisfy the relation, the arrangement period S1≠the fluctuation period 1/FSG. However, the example of FIG. 19 is more preferable than the example of FIG. 20. The reason is as follows. In the example of FIG. 19, the arrangement period S1 of the measuring pixels 65 is seven, and the fluctuation period 1/FSG is four, so these two numbers are relatively prime. In contrast, in the example of FIG. 20, the arrangement period S1 of the measuring pixels 65 is six, and the fluctuation period 1/FSG is four, so these two numbers are not relatively prime.

An overlapping manner of the X-ray absorbing section 33 and the plural measuring pixels 65 changes according to a position of each of the measuring pixels 65. For example, a certain measuring pixel 65 largely overlaps with the X-ray absorbing section 33, and another measuring pixel 65 has lower quantity of overlap. However, since both the X-ray absorbing section 33 and the measuring pixels 65 are periodically arranged, there becomes a cycle C of overlapping manner, in which a state of overlapping circles and becomes the same again. The cycle C of overlapping manner becomes the least common multiple of the pixel period of the arrangement period S1 and the pixel period of the fluctuation period 1/FSG. As the cycle C of overlapping manner becomes longer, the number of measuring pixels 65 included in the cycle C becomes larger. As the number of measuring pixels 65 included in cycle C becomes larger, an output value of each of the measuring pixels 65 disperses more. Accordingly, the average of output value of the each measuring pixel 65 can be equalized and a stable AEC can be performed.

In case of the example of FIG. 20, the cycle C of overlapping manner becomes the least common multiple (12) of the arrangement period S1(6) and the fluctuation period 1/FSG(4). In the example of FIG. 20, since the arrangement period S1 of the measuring pixels 65 (6) and the fluctuation period 1/FSG(4) are not relatively prime, the cycle C of overlapping manner is smaller than the product (4×6=24) of the arrangement period S1(6) and the fluctuation period 1/FSG(4). In the example of FIG. 20, the number of measuring pixels 65 included in the cycle C becomes two, which is calculated by division of the least common multiple (12) by the pixel period (6) of the arrangement period S1.

On the other hand, in the example of FIG. 19, since the arrangement period S1 of the measuring pixels 65 (7) and the fluctuation period 1/FSG(4) are relatively prime, the least common multiple becomes 7×4=28 so that the cycle C of overlapping manner becomes 28. Therefore, the cycle C of overlapping manner becomes equal to the product (7×4=28) of the arrangement period S1(7) and the fluctuation period 1/FSG(4). In the example of FIG. 19, the number of measuring pixels 65 included in the cycle C becomes four, which is calculated by division of the least common multiple (28) by the pixel period (7) of the arrangement period S1.

In comparing the examples of FIGS. 19 and 20, the cycle C (28) of FIG. 19 that is relatively prime becomes longer than the cycle C (12) of FIG. 20 that is not relatively prime. Accordingly, the number (4) of the measuring pixels 65 included in the cycle C of FIG. 19 becomes larger than the number (2) of the measuring pixels 65 included in the cycle C of FIG. 20. Because the cycle C of overlapping manner circulates, output values of the measuring pixels 65 highly disperse as the number of the measuring pixels 65 included in the cycle C increases. Therefore a fluctuation range of average of output values of the measuring pixels 65 becomes easier to be suppressed. Accordingly, like the example of FIG. 19, it is preferable that the arrangement period S1 and the fluctuation period 1/FSG are relatively prime.

In the following, other embodiments of the detection panel 35a will be explained. Regarding the configurations of each embodiment which are the same as the first and second embodiments, the same reference numerals are assigned and detailed explanations are omitted.

Third Embodiment

In a third embodiment illustrated in FIGS. 21A to 23, an arrangement of groups of the measuring pixels 65 which calculate average value of dose measuring signals of the measuring pixels 65 is determined as one set 200, and the plurality of sets 200 are periodically arranged in the same row and other rows. In this way, the sets 200 are dispersed in the whole area of the imaging surface 36. The set 200 is the minimum unit of the group of measuring pixels 65 for calculating the average value of dose measuring signals of the measuring pixels 65 in the AEC section 67. Note that it is not necessary to arrange the sets 200 throughout the whole area of the imaging surface 36. For example, the sets 200 may be arranged intensively in a region corresponding to the predetermined measurement area such as a bilateral lung field.

Figure 21A:
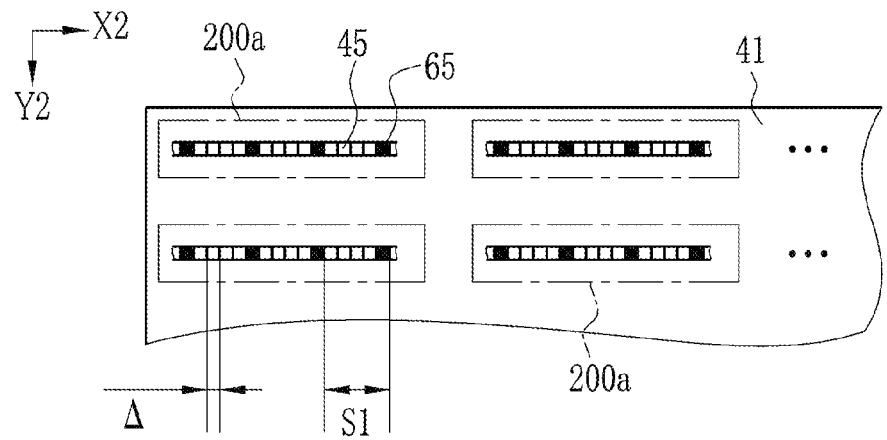
FIG. 21A is an explanatory view of a first state of a first example of a third embodiment.

In the example of FIG. 21A, the plurality of measuring pixels 65 (four in this example) are arranged in one line of the X2 direction, with the arrangement period S1=5. Sets 200a are periodically arranged, for example, with regular intervals. The set 200a is the minimum unit of the group of measuring pixels 65 for calculating the average value of dose measuring signals of the measuring pixels 65 in the AEC section 67. Note that the minimum unit for calculating the average value may be a block 201a illustrated in FIG. 21B which has the eight measuring pixels 65 formed in the two sets 200a, or a block 201b illustrated in FIG. 21C which has the twelve measuring pixels 65 formed in the three sets 200a. In addition, it may be that intervals between the sets 200a or between the blocks 201a and 201b are irregular.

Figure 21B:
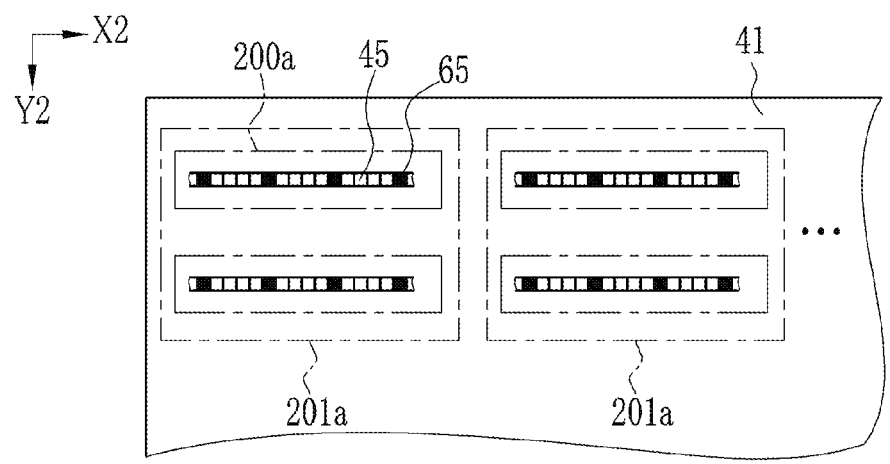
FIG. 21B is an explanatory view of a second state of the first example of the third embodiment.
Figure 21C:
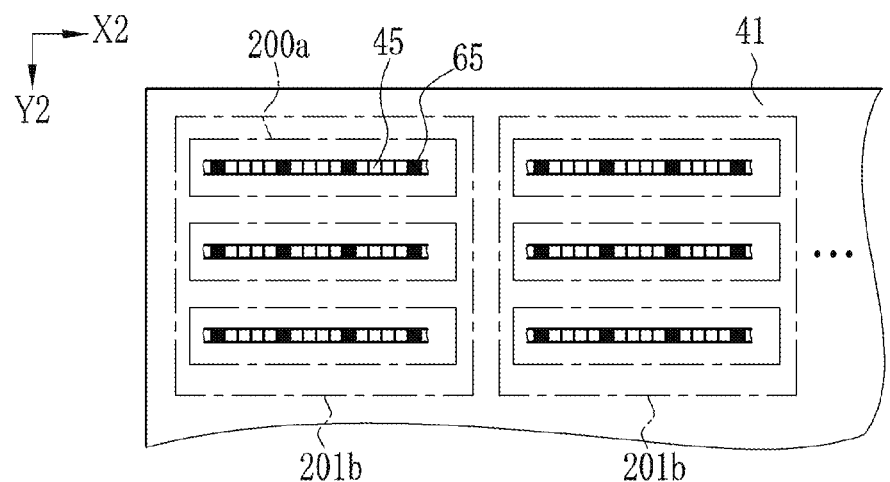
FIG. 21C is an explanatory view of a third state of the first example of the third embodiment.
Figure 22:
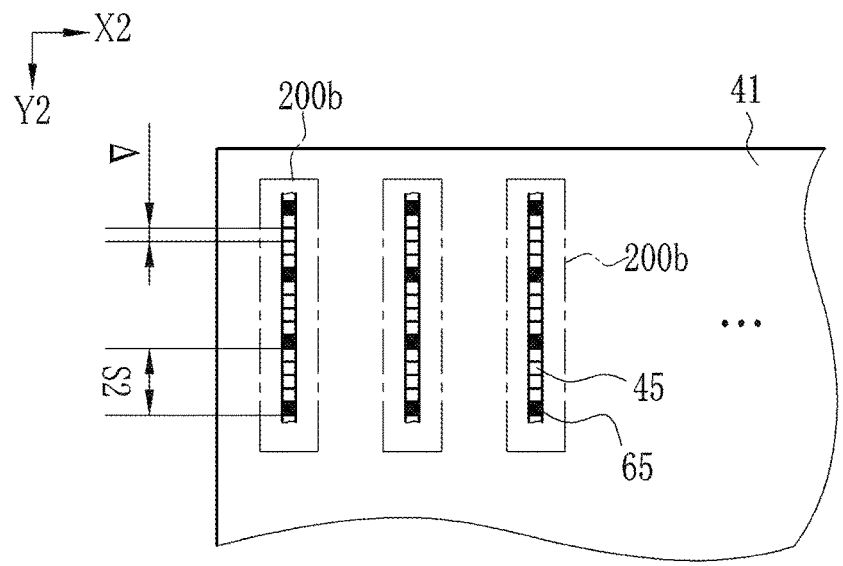
FIG. 22 is an explanatory view of a second example of the third embodiment.

In addition, sets 200b illustrated in FIG. 22, in which the arrangement direction of the measuring pixels 65 is the Y2 direction, may be used. In the set 200b, a pixel pitch Δ and an arrangement period S2 of the measuring pixels 65 are lengths in the Y2 direction. In addition, in the imaging surface 36, there may be a mixture of the sets 200a of the FIG. 21A to 21C in which the arrangement direction of the measuring pixels 65 goes along the X2 direction and the sets 200a of the FIG. 22 arranged along the Y2 direction. By properly using the sets 200a and 200b according to the attachment orientation of the grid 18, a stable AEC can be performed in each attachment orientation.

The set 200a in FIGS. 21A to 21C and the set 200b in FIG. 22 are composed of the plural measuring pixels 65 arranged along one column or one line. However, like sets 200c illustrated in FIG. 23, a set can be composed of the plural measuring pixels 65 which are arranged with being shifted in the X2 direction and the Y2 direction.

Figure 23:
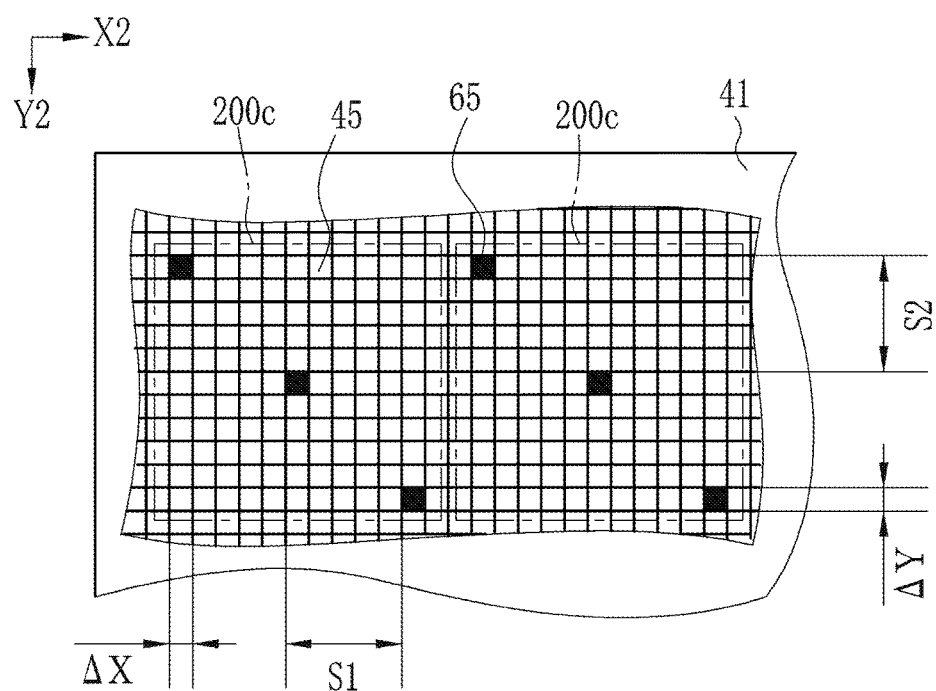
FIG. 23 is an explanatory view of a third example of the third embodiment.

In the set 200c in FIG. 23, the plurality of measuring pixels 65 are arranged with the arrangement period S1=5, with an interval corresponding the four lines in the X2 direction, though each of them are located in a different line. Even if lines in which the each measuring pixel 65 is located are different, only if the fluctuation period 1/FSG of the grid detection signal SG is different from the arrangement period S1 of the X2 direction, an output value of each of measuring pixels 65 disperses. Accordingly a fluctuation range of average values can be suppressed. In this way, even in the case that the each of the measuring pixels 65 is placed in the different line, the length of the X2 direction (line direction) becomes the arrangement period S1 of the measuring pixels 65, like the case that the plural measuring pixels 65 are arranged in one line.

Regarding the X2 direction, a pixel pitch ΔX and the arrangement period S1 of the measuring pixels 65 in the set 200c are the same as the pixel pitch Δ and the arrangement period S1 of the measuring pixels 65 in the set 200a in FIGS. 21A to 21C. Therefore, the average of output values of a group of the measuring pixels 65 in the set 200c becomes about the same with the average of output values of a group of measuring pixels 65 in the set 200a. Accordingly the set 200c may be provided in substitution for the set 200a.

The plurality of measuring pixels 65 in the set 200c are arranged with the arrangement period S2=5 in the Y2 direction, though each of them are located in a different row. Even if rows in which the each measuring pixel 65 is located are different, only if the fluctuation period 1/FSG of the grid detection signal SG is different from the arrangement period S1 of the Y2 direction, an output value of each of measuring pixels 65 disperses. Accordingly a fluctuation range of average values can be suppressed. Regarding the Y2 direction, a pixel pitch ΔY and the arrangement period S2 of the measuring pixels 65 in the set 200c are the same as the pixel pitch Δ and the arrangement period S2 of the measuring pixels 65 in the set 200b in FIG. 22. Accordingly the set 200c may be provided in substitution for the set 200b. In this way, even in the case that the each of the measuring pixels 65 is placed in the different row, the length of the Y2 direction (row direction) becomes the arrangement period S2 of the measuring pixels 65, like the case that the plural measuring pixels 65 are arranged in one row.

In addition, the set 200c is available for both of the set 200a in FIGS. 21A to 21C and the set 200b in FIG. 22. Accordingly, a stable AEC can be performed regardless of an attachment orientation of the grid 18 if the set 200c is provided, as same as the case of the mixture of the set 200a and the set 200b. Furthermore, in the case of using the mixture of the sets 200a and 200b, usage of each of the sets 200a and 200b needs to be changed according to an attachment orientation of the grid 18. However, in the case of using the set 200c, there is no need to adjust an attachment orientation of the grid 18. In addition, in the case of using the set 200c, the number of the measuring pixels 65 can be reduced to half in comparison with the case of using the mixture of sets 200a and 200b.

In addition, in case that the TFT and the signal line 52 are directly connected like the measuring pixels 65 of this embodiment, electric charge of the measuring pixels 65 flows constantly through the signal line 52. Therefore, even if the rows where each of the measuring pixels 65 is placed are different, timings of flowing electric charge of the measuring pixel 65 into the integration amplifiers 60 in the signal processing circuit 54 hardly change. Accordingly, there is the merit to be able to retrieve dose measuring signal of each of the measuring pixels 65 in the set 200c in the same timing.

Note that the set 200c in this example, the shift amounts regarding the X2 direction and the Y2 direction of the measuring pixels 65 are the same (for 5 pixels). However, the shift amounts may be changed according to the X2 direction and the Y2 direction.

Fourth Embodiment

Figure 24:
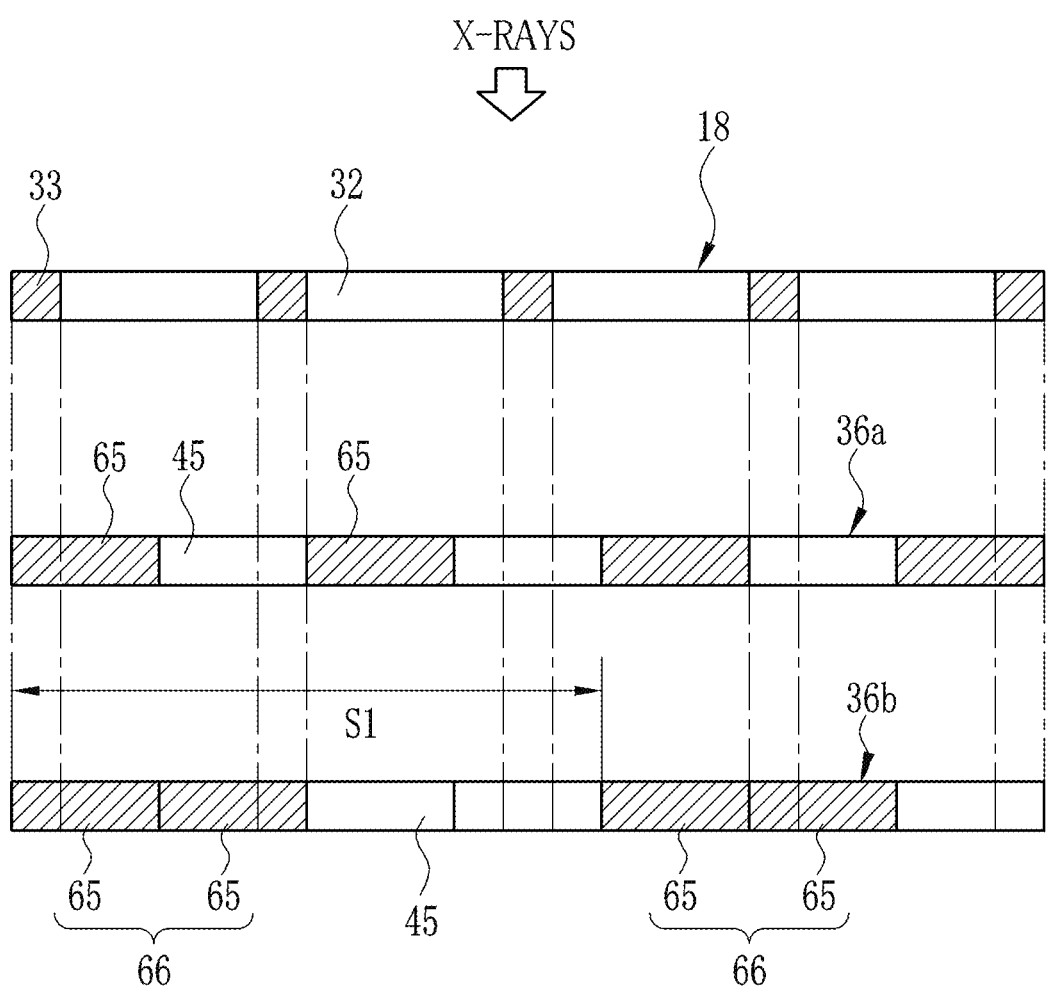
FIG. 24 is an explanatory view of a measuring pixel group of a fourth embodiment.

In the above embodiments, one dose measuring sensor is composed of one measuring pixel. However, as illustrated in FIG. 24, one dose measuring sensor may be composed of a measuring pixel group 66 consisting of adjacent plural measuring pixels 65. In case that the dose measuring sensor is constituted of the measuring pixel group 66, the arrangement period S1 is an arrangement period of the plurality of measuring pixel groups 66 which are arranged periodically with an interval.

FIG. 24 illustrates a state of the grid 18 and the imaging surface 36 of the detection panel 35a viewed from the lateral side (Y1, Y2 direction), like FIG. 8. The imaging surface 36a represents the case in which each of the measuring pixels 65 is used as the dose measuring sensor, and the imaging surface 36b represents the case in which the measuring pixel group 66 consisting of the two adjacent measuring pixels 65 is used as the dose measuring sensor. The measuring pixel 65 and the X-ray absorbing section 33 are distinguished from each other by hatching.

For example, in case that a width in the X1 direction of the X-ray transmitting section 32 and the X-ray absorbing section 33 of the grid 18 is 50 μm and 200 μm each, and a width in the same direction of measuring pixels 65 is 150 μm, a ratio of the X-ray transmitting section 32 to the area of the measuring pixels 65 of the imaging surface 36a becomes in a range of two-thirds to one, and a ratio of the X-ray transmitting section 32 to the area of the measuring pixel groups 66 of the imaging surface 36b becomes in a range of four-sixths to five-sixths. When X-ray of the same dose is detected in these area ratio, the maximum output difference between the maximum output value and the minimum output value of each of the measuring pixels 65 and the measuring pixel groups 66 becomes 1÷⅔=1.5 in the measuring pixels 65 of the imaging surface 36a, and becomes ⅚÷⅘=1.25 in the measuring pixel groups 66 of the imaging surface 36b.

As described above, when the measuring pixel group 66 is used as the dose measuring sensor, the maximum output difference of the dose measuring signals becomes smaller than the case in which one measuring pixel 65 is used as one dose measuring sensor. The fluctuation range of output values becomes smaller as the maximum output difference becomes smaller. Accordingly, even when a geometric layout of the grid 18 and the detection panel 35a shifts, a fluctuation range of output values of the each measuring pixel group 66 becomes smaller than that of the one measuring pixel 65. Accordingly, output values become stable, and a stable AEC which is not affected by shift of a geometric layout becomes enabled. In addition, as the measuring pixel group 66 has a larger area than the one measuring pixel 65, an amount of the dose measuring signal increases, and a signal-to-noise ratio improves. In addition, in the case that one dose measuring sensor is constituted of one measuring pixel group 66, it is preferable that the number of pixels constituting the measuring pixel group 66 is in the extent that human cannot recognize by sight when a defect correction is executed, specifically, for example 10 pixels. In this size, picture quality of an X-ray image does not decrease, since it is much smaller than the dose measuring sensor of U.S. Pat. No. 6,952,465, which has a stripe shape with the length for 500 pixels.

In the example of FIG. 24, the measuring pixel group 66 is constituted of the plural measuring pixels 65 adjacent in the X2 direction. However, the measuring pixel group 66 may be constituted of the plural measuring pixels 65 adjacent in the Y2 direction, or may be constituted of the plural measuring pixels 65 adjacent both in the X2 and Y2 directions. In addition, in the case that one dose measuring sensor is constituted of one measuring pixel group 66, the arrangement periods S1, S2 are an interval of two measuring pixel groups 66 as illustrated in FIG. 24. In the case of FIG. 24, the arrangement periods S1, S2 become four.

In the above embodiments, since the pixels 45 for image detection and the measuring pixels 65 functioning as the dose measuring sensors are independent from each other, and reading from the measuring pixel 65 is destructive read-out, the part of the measuring pixel 65 becomes a so-called point defect. However, since the size of one pixel is small enough, it is found out by an experiment that the defect becomes hard to be recognized by human eye by executing a defect correction by which the pixel value corresponding to the position of the measuring pixel 65 is interpolated with the pixel value of the normal pixel 45 adjoining to the measuring pixel 65. Accordingly there is no substantial problem. However, since it is preferable that there is no point defect, a detection panel 100 having structure as illustrated in FIG. 25 can be used to eliminate the need for the defect correction.

Fifth Embodiment

Figure 25:
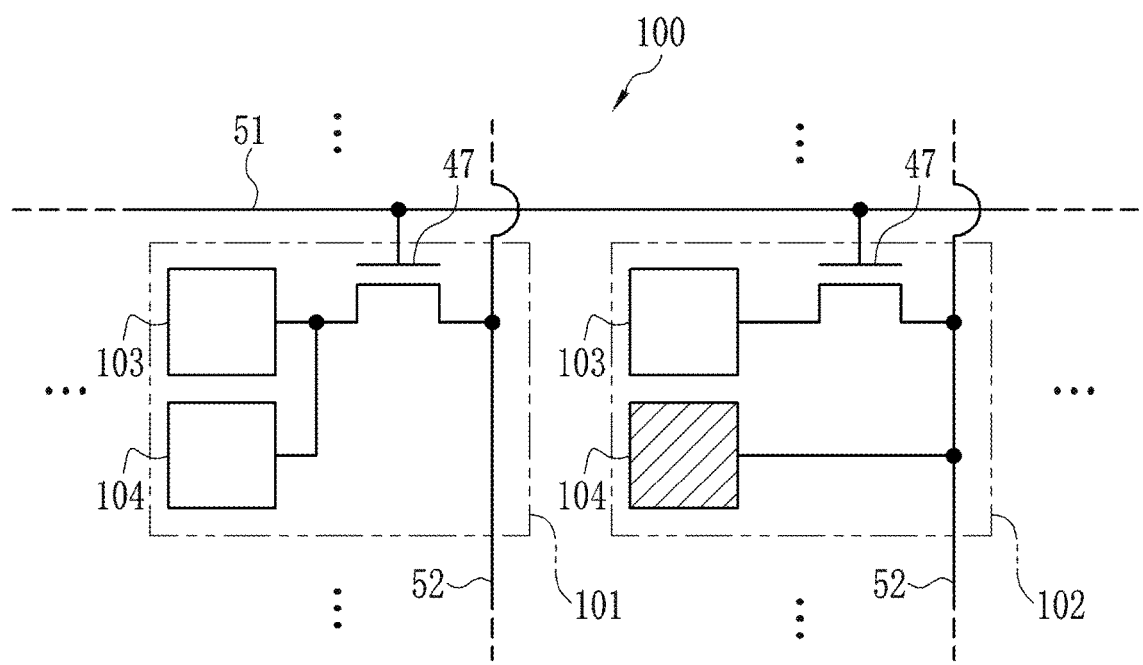
FIG. 25 is an explanatory view of a detection panel of a fifth embodiment.

In FIG. 25, the detection panel 100 includes first pixels 101 for specific use in image detection and second pixels 102 for use in the image detection and the AEC. The first and second pixels 101 and 102 are arranged into a matrix at an appropriate ratio, as with the pixels 45 and the measuring pixels 65 of the above embodiment. The arrangement period of the second pixels 102 is different from the arrangement period of the X-ray absorbing section 33 of the grid 18. Each of the first pixel 101 and the second pixel 102 has two photodiodes 103 and 104. The photodiodes 103 and 104 of the first pixel 101 are connected in parallel, and one end is connected to the signal line 52 through the TFT 47. In the second pixel 102, on the other hand, an end of the photodiode 103 is connected to the signal line 52 through the TFT 47, but the photodiode 104 is directly connected to the signal line 52 without through the TFT 47. In other words, the photodiode 104 of the second pixel 102 has the same structure as the measuring pixel 65 of the above embodiments.

From the first pixel 101, electric charge accumulated in the two photodiodes 103 and 104 is read out. From the second pixel 102, on the other hand, electric charge accumulated only in the photodiode 103 is read out. The photodiode 104 of the second pixel 102 is used for the AEC and does not contribute the production of the X-ray image. Accordingly, in a case where the same X-ray dose is applied to the photodiodes 103 to 104 of the same size, the pixel value of the second pixel 102 is approximately a half of that of the first pixel 101. However, the deterioration in the image quality of the X-ray image is prevented as compared with the above embodiments which require the defect correction since the pixel value cannot be obtained from the position of the measuring pixel 65. The X-ray image can be produced without the defect correction by multiplying the output of the second pixel 102 by a coefficient, which is calculated in advance based on the size of the photodiodes 103 to 104. This almost completely eliminates an adverse effect on the X-ray image quality that is caused by providing the pixels for specific use in the AEC.

Sixth Embodiment

Figure 26:
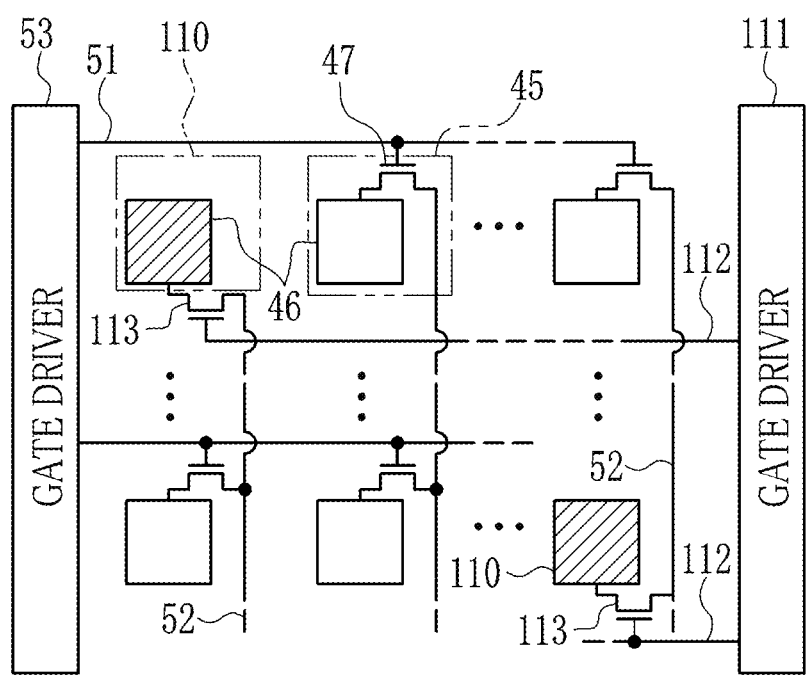
FIG. 26 is an explanatory view of a detection panel of a sixth embodiment.

In the first embodiment, the measuring pixel 65 that is directly connected to the signal line 52 without through the TFT 47 is used as the dose measuring sensor. However, as illustrated in FIG. 26, a measuring pixel 110 may be connected to a TFT 113 driven by a gate driver 111 and a scan line 112 that are different from these of the pixel 45. Electric charge accumulated in the measuring pixel 110 can be read out independently of that in the pixel 45.

Seventh Embodiment

Alternatively, with taking advantage of the fact that electric current flowing through the bias line 48 for supplying the bias voltage Vb to each pixel 45 is in proportion to the amount of the electric charge produced in the pixel 45, the electric current flowing through the bias line 48 connected to the specific pixel may be monitored to detect the X-ray dose. In another case, the X-ray dose may be measured based on leak current from the normal pixels 45 in a state where all the TFTs 47 are turned off. In further another case, another AEC measuring pixel that has different structure from the pixel 45 may be provided on the same plane with the imaging surface 36 separately. The same plane includes any plane which is parallel to a TFT active matrix substrate which is perpendicular to the X-ray incidence direction, such as a plane as a different layer for AEC superimposed on the TFT active matrix substrate on which the TFT 47 is provided, and a plane provided at the other side of a scintillator from the TFT 47. However, it is preferable that a size of the dose measuring sensor dedicated for an AEC is in the extent that the sensor does not visible, specifically, a size of around 10 pixels.

In the above embodiments, it is explained the example in which the average value of the output values of the plural dose measuring sensors is calculated in AEC, and the emission stop threshold value is compared with the integrated value of the average values. However, in substitution for the average value of output values of the plural dose measuring sensors, mean value and total value may be calculated, and the emission stop threshold value may be compared with the integrated value of mean values or the total values. According to the present invention, since output values of the plural dose measuring sensors disperse, even if mean values or total values are used, the same effect as in the case of average values can be obtained.

In the above embodiments, the electronic cassette which is the X-ray image detecting device of portable type is explained as the example. However, the present invention may apply to an X-ray image detecting device of stand-alone type incorporated in an imaging stand. In addition, the example that the console 17 and the electronic cassette 16 are separately provided is explained. However, the console 17 does not have to be an independent device, and the function of the console 17 may be incorporated in the electronic cassette 16. And there may be an unified device of the source controller 14 and the console 17.

In the above embodiments, it is described about the case that the positions of the measuring pixels 65 are known at the time of manufacture of the image detection section 35, and the image detection section 35 memorizes the positions (coordinates) of all the measuring pixels 65 beforehand in an internal memory (not illustrated). However, the present invention is not limited to this example. Specifically, it may be that all pixels 45 are constituted so that a non destructive read-out can be executed, and pixels to be used as the measuring pixels are occasionally selected from all of the pixels 45 for read-out of output values. For example, it may be constituted that the pixels 45 in a corresponding location is selected occasionally as the measuring pixels when a part to be photographed is selected through a photography menu, and the fluctuation period FSG of the grid detection signal SG does not accord with the arrangement periods S1, S2 of the measuring pixels or the measuring pixel groups at that time.

The present invention can be applied to a photography system using not only X-ray but also other radiation such as gamma ray.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image detecting device being able to perform photography with using an anti-scatter grid where radiation absorbing sections which absorb radiation and radiation transmitting sections which transmit radiation are arranged in a periodic alternating manner in a first direction, said radiation image detecting device comprising:
    a detection panel having an imaging surface where plural pixels for receiving radiation from a radiation source are provided, a radiation image of an object being detected by said pixels receiving radiation which penetrated an object; and
    a plurality of dose measuring sensors provided to perform exposure control of said radiation image, being arranged in said imaging surface in said first direction periodically with keeping a space, and detecting radiation dose which penetrated said object to output a signal depending on said dose,
    wherein said plural dose measuring sensors are arranged so that an arrangement period of said plural dose measuring sensors in said first direction in said imaging surface differs from a fluctuation period of a grid detection signal representing an image of said anti-scatter grid which is obtained when radiation is irradiated equally to said imaging surface and said anti-scatter grid is photographed by said detection panel, an output value of said grid detection signal fluctuating periodically by reflecting an arrangement state in said first direction of said radiation absorbing section and said radiation transmitting section.

2. The radiation image detecting device according to claim 1,
    wherein said arrangement period of said dose measuring sensors is not an integral multiple of said fluctuation period of said grid detection signal.

3. The radiation image detecting device according to claim 1,
    wherein said arrangement period of said dose measuring sensors and said fluctuation period of said grid detection signal are relatively prime.

4. The radiation image detecting device according to claim 1,
    wherein said arrangement period of said dose measuring sensors is different from said fluctuation period of said grid detection signal also in a second direction which is perpendicular to said first direction.

5. The radiation image detecting device according to claim 4,
    wherein said arrangement period of said dose measuring sensors in said first direction and said arrangement period of said dose measuring sensors in said second direction are the same.

6. The radiation image detecting device according to claim 1,
    wherein the minimum size of said single dose measuring sensor is the same as a size of said pixel in said imaging surface.

7. The radiation image detecting device according to claim 1,
    wherein a pixel pitch of said pixels is larger than half of a grid pitch which is the width of one set of said radiation absorbing section and said radiation transmitting section in said anti-scatter grid.

8. The radiation image detecting device according to claim 1,
    wherein said dose measuring sensors are measuring pixels using a part of said pixels.

9. The radiation image detecting device according to claim 4,
    wherein said dose measuring sensors are measuring pixels using a part of said pixels, and
    wherein said plural measuring pixels are arranged in a line direction corresponding to said first direction and a column direction corresponding to said second direction with an interval corresponding to at least one line or one column in the each direction, and said arrangement period in said first direction is an interval length in said line direction, and said arrangement period in said second direction is an interval length in said column direction.

10. The radiation image detecting device according to claim 8, wherein said single dose measuring sensor is a measuring pixel group consisting of a plurality of adjacent said measuring pixels.

11. The radiation image detecting device according to claim 10,
wherein said arrangement period is an arrangement period of a plurality of said plural measuring pixel groups which are arranged periodically with an interval.

12. The radiation image detecting device according to claim 1,
wherein said dose measuring sensor outputs a signal corresponding to a dose per unit time, and
wherein said radiation image detecting device further comprises an automatic exposure controller which multiplies output values from said dose measuring sensors, compares said multiplied integrated value with a predetermined emission stop threshold value, and stops irradiation of radiation from said radiation source when said integrated value reaches said emission stop threshold value.

13. The radiation image detecting device according to claim 12,
wherein said automatic exposure controller calculates the average value of output values from said plural dose measuring sensors, and multiplies said calculated average values to obtain said integrated value.

14. The radiation image detecting device according to claim 1,
wherein said anti-scatter grid is detachably attached to said radiation image detecting device.

15. A radiation imaging system being able to perform photography with using an anti-scatter grid where radiation absorbing sections which absorb radiation and radiation transmitting sections which transmit radiation are arranged in a periodic alternating manner in a first direction, said radiation imaging system comprising:
 a radiation generator including a radiation source for irradiating radiation; and
 a radiation image detecting device for detecting a radiation image,
 said radiation image detecting device including:
 a detection panel having an imaging surface where plural pixels for receiving radiation from a radiation source are provided, a radiation image of an object being detected by said pixels receiving radiation which penetrated an object; and
 a plurality of dose measuring sensors provided to perform exposure control of said radiation image, being arranged in said imaging surface in said first direction periodically with keeping a space, and detecting radiation dose which penetrated said object to output a signal depending on said dose,
 wherein said plural dose measuring sensors are arranged so that an arrangement period of said plural dose measuring sensors in said first direction in said imaging surface differs from a fluctuation period of a grid detection signal representing an image of said anti-scatter grid which is obtained when radiation is irradiated equally to said imaging surface and said anti-scatter grid is photographed by said detection panel, an output value of said grid detection signal fluctuating periodically by reflecting an arrangement state in said first direction of said radiation absorbing section and said radiation transmitting section.

* * * * *